United States Patent
Takahashi et al.

(10) Patent No.: US 7,879,583 B2
(45) Date of Patent: *Feb. 1, 2011

(54) PROCESS FOR PRODUCING L-GLUTAMIC ACID

(75) Inventors: Yusuke Takahashi, Kawasaki (JP); Yasuhiro Tateyama, Kawasaki (JP); Masakazu Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 432 days.

This patent is subject to a terminal disclaimer.

(21) Appl. No.: 12/033,374

(22) Filed: Feb. 19, 2008

(65) Prior Publication Data

US 2010/0003726 A1    Jan. 7, 2010

Related U.S. Application Data

(63) Continuation of application No. 11/297,383, filed on Dec. 9, 2005, now Pat. No. 7,354,744, which is a continuation of application No. PCT/JP2004/008140, filed on Jun. 10, 2004.

(30) Foreign Application Priority Data

Jun. 10, 2003   (JP) .............................. 2003-165545

(51) Int. Cl.
    *C12P 13/14*    (2006.01)
(52) U.S. Cl. ..................................... 435/110
(58) Field of Classification Search ....................... None
    See application file for complete search history.

(56) References Cited

U.S. PATENT DOCUMENTS

| 6,197,559 | B1 | 3/2001 | Moriya et al. |
| 6,331,419 | B1 | 12/2001 | Moriya et al. |
| 6,596,517 | B2 | 7/2003 | Izui et al. |
| 6,653,110 | B2 | 11/2003 | Sato et al. |
| 7,354,744 | B2 * | 4/2008 | Takahashi et al. ........... 435/110 |

FOREIGN PATENT DOCUMENTS

| EP | 0 999 282 | 5/2000 |
| EP | 1 078 989 | 2/2001 |
| EP | 1 382 686 | 1/2004 |
| EP | 1 352 966 | 7/2005 |
| EP | 1 233 069 | 9/2005 |
| JP | 61-139398 | 6/1986 |

OTHER PUBLICATIONS

International Search Report for PCT Patent App. No. PCT/JP2004/008140 (Jul. 20, 2004).
International Report on Patentability for PCT Patent App. No. PCT/JP2004/0084140 (May 11, 2006).

* cited by examiner

*Primary Examiner*—Herbert J. Lilling
(74) *Attorney, Agent, or Firm*—Shelly Guest Cermak; Cermak Nakajima LLP

(57) ABSTRACT

L-glutamic acid is produced by culturing a microorganism in a liquid medium containing L-glutamic acid at a saturation concentration, wherein the microorganism can metabolize a carbon source at a specific pH, and also has an ability to accumulate L-glutamic acid in the medium in an amount which exceeds the saturation concentration of L-glutamic acid, wherein the pH of the medium is controlled so that L-glutamic acid precipitates.

16 Claims, 7 Drawing Sheets

PROCESS FOR PRODUCING L-GLUTAMIC ACID

The present invention is a continuation under 35 U.S.C. §120 of U.S. patent application Ser. No. 11/297,383, filed Dec. 9, 2005, now U.S. Pat. No. 7,354,744 which claims priority under 35 U.S.C. §119 to Japanese Patent Application No. 2003-165545, filed Jun. 10, 2003, which is a continuation under 35 U.S.C. §120 of PCT/JP2004/008140, filed Jun. 10, 2004, the entireties of which are incorporated by reference. Also, the Sequence Listing filed electronically herewith is hereby incorporated by reference (File name: US-256_Seq_List_Copy_1; File size: 83 KB; Date recorded: Feb. 19, 2008).

BACKGROUND OF THE INVENTION

1. Field of the Invention

The present invention relates to a method for producing L-glutamic acid by fermentation. L-glutamic acid is widely used as a raw material in the production of seasonings and so forth.

2. Description of the Related Art

L-glutamic acid is mainly produced by fermentation using an L-glutamic acid-producing bacterium of the so-called coryneform bacterium belonging to the genus *Brevibacterium, Corynebacterium* or *Microbacterium* or mutant strains thereof. Moreover, methods utilizing a microorganism belonging to the genus *Bacillus, Streptomyces, Penicillium, Pseudomonas, Arthrobacter, Serratia, Candida*, or *Aerobacter aerogenes* (currently *Enterobacter aerogenes*), a mutant strain of *Escherichia coli*, or the like are known. Furthermore, also known are methods of producing L-glutamic acid using a microorganism belonging to the genus *Klebsiella, Erwinia*, or *Pantoea* (U.S. Pat. No. 6,197,559), and methods of producing L-glutamic acid using an *Enterobacter* bacterium (U.S. Pat. No. 6,331,419).

Furthermore, various techniques for improving L-glutamic acid-producing ability by enhancing activities of L-glutamic acid biosynthetic enzymes through the use of recombinant DNA techniques have been disclosed. For example, it was reported that the introduction of a gene encoding citrate synthase derived from *Escherichia coli* or *Corynebacterium glutamicum* was effective for enhancing L-glutamic acid-producing ability in bacterium belonging to the genus *Corynebacterium* or *Brevibacterium* (Japanese Patent Publication (JP 7-121228 B). In addition, JP 61-268185 A discloses a cell harboring recombinant DNA containing a glutamate dehydrogenase gene derived from *Corynebacterium* bacteria. Furthermore, JP 63-214189 A discloses a technique for increasing L-glutamic acid-producing ability by amplifying genes encoding glutamate dehydrogenase, isocitrate dehydrogenase, aconitate hydratase, and a citrate synthase.

L-glutamic acid production has been considerably increased by the aforementioned breeding of microorganisms or improving production methods. However, in order to respond to increased demand in the future, the development of methods which provide more efficient production of L-glutamic acid at a lower cost are still necessary, and therefore, still represent a need in the art.

Methods for L-glutamic acid fermentation while precipitating L-glutamic acid, which accumulates in culture broth, have been developed (EP 1078989 A). Because the usual L-glutamic acid-producing bacteria cannot grow under acidic conditions, L-glutamic acid fermentation was conventionally performed under neutral conditions. Contrary to such conventional techniques, microorganisms which could produce L-glutamic acid under acidic conditions were screened, and it has been reported that L-glutamic acid can be produced and accumulated in the medium while precipitating the L-glutamic acid by culturing the obtained microorganism (*Enterobacter agglomerans*) in a liquid medium in which the pH is controlled so that L-glutamic acid is precipitated.

Furthermore, methods are known for producing L-glutamic acid by culturing such an L-glutamic acid-producing bacterium that can grow under acidic conditions as described above in a medium having a total content of organic acids that inhibit growth of the bacterium in an amount that does not inhibit the growth of the bacterium (European Patent Application Laid-open No. 1233070) and for producing L-glutamic acid by culturing such a bacterium as described above at a first pH optimal for growth of the microorganism and then culturing the bacterium at a second pH optimal for L-glutamic acid production by the microorganism and lower than the first pH (European Patent Application Laid-open No. 1233068). Furthermore, a method is known for producing and accumulating L-glutamic acid in a medium while precipitating the L-glutamic acid in the medium, wherein crystals of L-glutamic acid are made to exist in the medium while L-glutamic acid concentration in the medium is lower than the concentration at which natural crystallization of L-glutamic acid occurs (European Patent Application Laid-open No. 1233069).

SUMMARY OF THE INVENTION

An object of the present invention is to provide a method for more efficiently producing L-glutamic acid compared with prior art techniques by using a bacterium having an ability to produce L-glutamic acid such as a bacterium belonging to the genus *Pantoea*.

The inventors of the present invention found that if a high L-glutamic acid-producing ability was imparted to a bacterium belonging to the genus *Pantoea*, acetoin and 2,3-butanediol are also produced together with L-glutamic acid. Furthermore, they considered that if it became possible to suppress the production of these by-products, the yield of L-glutamic acid per unit amount of the main raw material (sugar) would be improved. Thus, the inventors of present invention conducted various research and, as a result, found that if pantothenic acid was added to a medium, the by-production of acetoin and 2,3-butanediol was reduced, and as a result, the fermentation yield of L-glutamic acid was improved. Thus, they accomplished the present invention.

That is, the objects of the present invention are as follows. It is an object of the present invention to provide a method for producing L-glutamic acid comprising culturing a microorganism belonging to the genus *Pantoea* in a medium which contains pantothenic acid, wherein the pH of the medium is controlled so to induce precipitation of L-glutamic acid, and collecting said L-glutamic acid from said medium.

It is a further object of the invention to provide the method as described above, wherein said microorganism is able to metabolize a carbon source in a second medium which contains L-glutamic acid at a saturation concentration and has an ability to cause accumulation of L-glutamic acid in said second medium, wherein said second medium is at a second pH.

It is a further object of the invention to provide the method as described above, wherein the microorganism is *Pantoea ananatis*.

It is a further object of the invention to provide the method as described above, wherein said pantothenic acid is a pantothenic acid salt, and the concentration of said salt is at least 1 mg/L.

DETAILED DESCRIPTION OF THE PREFERRED EMBODIMENTS

Figure 1:
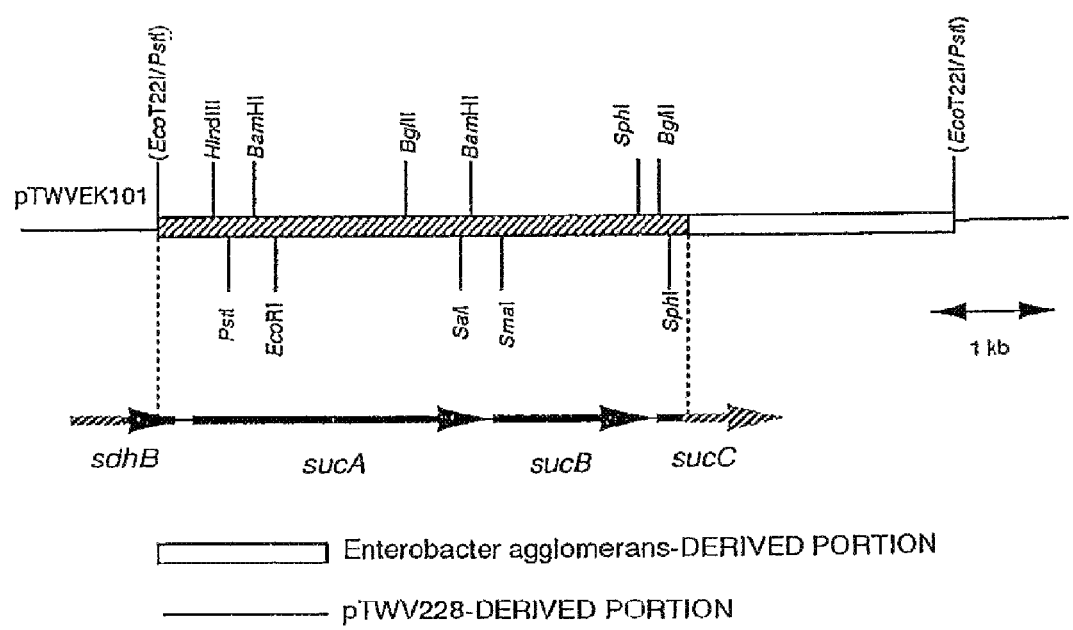
FIG. 1 shows a restriction map of a DNA fragment of pTWVEK101 derived from *Pantoea ananatis*.

Hereinafter, the present invention will be explained in detail.

The present invention provides a method for producing L-glutamic acid by fermentation by culturing a microorganism in a medium which contains pantothenic acid, wherein the pH of the medium is controlled so to induce precipitation of L-glutamic acid, and wherein said microorganism is able to metabolize a carbon source at a second pH in a second medium which contains L-glutamic acid at a saturation concentration, and wherein said microorganism has an ability to cause accumulation of L-glutamic acid in said second medium at said second pH, and wherein said L-glutamic acid accumulates in an amount exceeding the amount corresponding to the saturation concentration of L-glutamic acid (henceforth also referred to as an "L-glutamic acid-accumulating microorganism").

The above L-glutamic acid-accumulating microorganism can be obtained, for example, as follows. A sample containing microorganisms is inoculated into a liquid medium containing 1) L-glutamic acid at a saturation concentration and 2) a carbon source at a specific pH. A strain that is able to metabolize the carbon source is then selected. Although the specific pH is not particularly limited, it is usually about 5.0 or less, preferably about 4.5 or less, further preferably about 4.3 or less. The L-glutamic acid-accumulating microorganism is used for production of L-glutamic acid by fermentation with accompanying precipitation of the L-glutamic acid. If the pH is too high, it becomes difficult for the microorganism to produce L-glutamic acid in an amount sufficient for precipitation. Therefore, the pH is preferably in the aforementioned range.

If the pH of an aqueous solution containing L-glutamic acid is lowered, the solubility of L-glutamic acid significantly falls when the pH is about equal to the pKa of the γ-carboxyl group, or about 4.25 at 25° C. The solubility is the lowest at the isoelectric point (pH 3.2), and the amount of L-glutamic acid which exceeds the saturation concentration precipitates.

While it depends on the composition of the medium, L-glutamic acid is dissolved in an amount of 10-20 g/L at pH 3.2, 30-40 g/L at pH 4.0 and 50-60 g/L at pH 4.7, at about 30° C. Usually the pH does not need to be 3.0 or lower, because the L-glutamic acid precipitating effect reaches its upper limit when the pH falls below a certain value. However, the pH may be 3.0 or less.

In addition, the expression that a microorganism "can metabolize a carbon source" or "is able to metabolize a carbon source" means that the microorganism can proliferate or can consume a carbon source even though it cannot proliferate, that is, it indicates that the microorganism catabolizes a carbon source such as sugars or organic acids. Specifically, for example, if a microorganism proliferates when it is cultured in a liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can metabolize the carbon source in the medium. Furthermore, for example, if a microorganism consumes a carbon source even though the microorganism does not proliferate, when it is cultured in a synthetic liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can metabolize the carbon source in the medium.

The microorganism that can metabolize a carbon source includes a microorganism that can grow in the aforementioned liquid medium. The expression that a microorganism "can grow" means that it can proliferate, or it can produce L-glutamic acid even though it cannot proliferate. Specifically, for example, if a microorganism proliferates when it is cultured in a liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can grow in the medium. Furthermore, for example, if a microorganism increases the amount of L-glutamic acid in a synthetic liquid medium even though the microorganism does not proliferate, when the microorganism is cultured in the synthetic liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can grow in the medium.

The selection of a microorganism as described above may be repeated two or more times under the same conditions, or by changing the pH or the concentration of L-glutamic acid. Selection at an early stage can be performed in a medium containing L-glutamic acid at a concentration lower than the saturation concentration, and subsequent selection can be performed in a medium containing L-glutamic acid at the saturation concentration. Furthermore, strains with favorable properties, such as a superior proliferation rate, may be selected.

The L-glutamic acid-accumulating microorganism has an ability to cause accumulation of an amount of L-glutamic acid which exceeds the saturation concentration of L-glutamic acid in a liquid medium, in addition to the properties described above. The pH of the aforementioned liquid medium is preferably the same as or close to that of the medium used for screening a microorganism having the aforementioned properties. Usually, a microorganism becomes more sensitive to L-glutamic acid at a high concentration as the pH falls. Therefore, it is preferred that the pH is not low in view of resistance to L-glutamic acid, but a low pH is preferred for production of L-glutamic acid with accompanying precipitation. To satisfy these conditions, the pH can be in the range of 3 to 5, preferably 4 to 5, more preferably 4 to 4.7, further preferably 4 to 4.5, particularly preferably 4.0 to 4.3.

Examples of the L-glutamic acid-accumulating microorganism or breeding materials thereof include, but are not limited to, microorganisms belonging to the genus *Pantoea, Enterobacter, Klebsiella, Serratia, Erwinia, Escherichia, Corynebacterium, Brevibacterium, Alicyclobacillus, Bacillus, Saccharomyces*, or the like. Of these, microorganisms belonging to the genus *Pantoea* are preferred. Hereinafter, the microorganism of the present invention will be explained mainly for microorganisms belonging to the genus *Pantoea*. However, the microorganism is not limited to those belonging to the genus *Pantoea*, and those belonging to other genera can be similarly used.

An example of a microorganism belonging to the *Pantoea* includes, but is not limited to, *Pantoea ananatis*, preferably *Pantoea ananatis* AJ13355. This strain was isolated from soil in Iwata-shi, Shizuoka, Japan, and can proliferate in a medium containing L-glutamic acid and a carbon source at low pH.

The *Pantoea ananatis* AJ13355 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary) on Feb. 19, 1998 and received an accession number of FERM P-16644. It was then converted to an international deposit under the provisions of Budapest Treaty on Jan. 11, 1999 and received an accession number of FERM BP-6614.

The above strain was identified as *Enterobacter agglomerans* when it was isolated and deposited as the *Enterobacter agglomerans* AJ13355 strain. However, it was recently re-classified as *Pantoea ananatis* on the basis of nucleotide sequencing of 16S rRNA and so forth (see the examples section).

Although the strains AJ13356 and AJ13601 that were derived from AJ13355 strain were also deposited at the aforementioned depository as *Enterobacter agglomerans*, they are described as *Pantoea ananatis* in this specification.

The L-glutamic acid-accumulating microorganism may originally have L-glutamic acid-producing ability, or may have L-glutamic acid-producing ability imparted or increased by breeding through mutagenesis, recombinant DNA techniques, or the like.

The L-glutamic acid-producing ability can be imparted or increased by, for example, increasing an activity of an enzyme that catalyzes a biosynthetic reaction of L-glutamic acid. The L-glutamic acid-producing ability can also be increased by decreasing or eliminating activity of an enzyme that catalyzes a reaction which branches off from the biosynthetic pathway of L-glutamic acid, and generates a compound other than L-glutamic acid.

Examples of the enzyme that catalyzes the biosynthetic reaction of L-glutamic acid include, but are not limited to, glutamate dehydrogenase (hereinafter, also referred to as "GDH"), glutamine synthetase, glutamate synthase, isocitrate dehydrogenase, aconitate hydratase, citrate synthase (hereafter, also referred to as "CS"), phosphoenolpyruvate carboxylase (hereinafter, also referred to as "PEPC"), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase, and so forth. Of these enzymes, one or any combination of CS, PEPC, and GDH are preferred. Furthermore, it is preferred that the activities of all the three of the enzymes CS, PEPC, and GDH, are enhanced in the L-glutamic acid-accumulating microorganism. In particular, CS from *Brevibacterium lactofermentum* is preferred, because it is not subject to inhibition by α-ketoglutaric acid, L-glutamic acid, and NADH.

In order to enhance the activity of CS, PEPC or GDH, for example, a gene encoding CS, PEPC or GDH can be cloned on an appropriate plasmid and transformed into a host microorganism. The copy number of the gene encoding CS, PEPC, or GDH (hereinafter, abbreviated as "gltA gene", "ppc gene", and "gdhA gene", respectively) in the transformant can be increased, resulting in an increase in the activity of CS, PEPC, or GDH.

The cloned gltA, ppc, and gdhA genes are introduced into the aforementioned starting parent strain solely or randomly in combination. When two or three kinds of the genes are introduced, they may be cloned on one plasmid and introduced into the host, or separately cloned onto two or three different plasmids that can coexist, and then introduced into the host.

Two or more genes encoding the same enzyme, but derived from different microorganisms, may be introduced into the same host.

The plasmids described above are not particularly limited so long as they are autonomously replicable in a microorganism belonging to, for example, the genus *Pantoea* or the like. Examples of these plasmids include pUC19, pUC18, pBR322, pHSG299, pHSG298, pHSG399, pHSG398, RSF1010, pMW119, pMW118, pMW219, pMW218, pACYC177, pACYC184, and so forth. Vectors of phage DNA can also be used for introducing the aforementioned genes.

Transformation can be performed by, for example, the method of D. M. Morrison (Methods in Enzymology, 68, 326 (1979)), wherein permeability of recipient bacterium cells is increased by treating the cells with calcium chloride (Mandel M. and Higa A., J. Mol. Biol., 53, 159 (1970)), electroporation (Miller J. H., "A Short Course in Bacterial Genetics", Cold Spring Harbor Laboratory Press, U.S.A., 1992), or the like.

The activity of CS, PEPC or GDH can also be increased by allowing multiple copies of the gltA gene, the ppc gene, or the gdhA gene to be present on chromosomal DNA of the aforementioned starting parent strain. Multiple copies of the gltA gene, the ppc gene, or the gdhA gene may be introduced into the chromosomal DNA by homologous recombination. In order to introduce multiple copies of these genes into the chromosomal DNA of a bacterium belonging to the genus *Pantoea*, sequences can be used which are present on the chromosomal DNA in multiple copy number, such as a repetitive DNA and inverted repeats present at the end of a transposable element. Alternatively, multiple copies of the gltA gene, the ppc gene, or the gdhA gene can be introduced into the chromosomal DNA by incorporating them into a transposon and transferring it. As a result, the copy number of gltA gene, the ppc gene, or the gdhA gene in a transformant strain is increased, and thus the activity of CS, PEPC, or GDH is increased.

As organisms used as a source of the gltA gene, the ppc gene, or the gdhA gene of which copy number is to be increased, any organism can be used so long as it has activity of CS, PEPC, or GDH. Examples of the organism preferably include, but are not limited to, bacteria belonging to the genus *Pantoea, Enterobacter, Klebsiella, Erwinia, Serratia, Escherichia, Corynebacterium, Brevibacterium*, or *Bacillus*. Specifically, *Escherichia coli, Brevibacterium lactofermentum* and so forth are encompassed by the present invention. The gltA gene, the ppc gene, and the gdhA gene can be obtained from chromosomal DNA of the microorganisms described above.

The gltA gene, the ppc gene, and the gdhA gene can be obtained using a mutant strain which is deficient in the activity of CS, PEPC, or GDH so that a DNA fragment is isolated that supplements its auxotrophy from the chromosomal DNA of the aforementioned microorganism. Furthermore, since the nucleotide sequences of these genes from bacteria belonging to the genera *Escherichia* and *Corynebacterium* are known (Biochemistry, 22, pp. 5243-5249, (1983); J. Biochem., 95, pp. 909-916, (1984); Gene, 27, pp. 193-199, (1984); Microbiology, 140, pp. 1817-1828, (1994); Mol. Gen. Genet., 218, pp. 330-339, (1989); Molecular Microbiology, 6, pp. 317-326, (1992)), they can also be obtained by PCR utilizing primers which have been synthesized based on each nucleotide sequence and using the chromosomal DNA as a template. It is known that, in enterobacteria such as bacteria belonging to the genus *Enterobacter* or *Klebsiella*, introduction of a gltA gene from a coryneform bacterium is more effective for enhancing the L-glutamic acid-producing ability when compared with that of a gltA gene from a bacterium of the same species (European Patent Application Laid-open No. 0999282). The strains of *Pantoea* ananatis described herein are described as *Enterobacter agglomerans*.

The activity of CS, PEPC, or GDH can also be increased by enhancing the expression of the gltA gene, the ppc gene, or the gdhA gene, besides the aforementioned amplification of the genes. For example, the expression can be enhanced by replacing a promoter for the gltA gene, the ppc gene, or the gdhA gene with a stronger promoter. For example, lac promoter, trp promoter, trc promoter, tac promoter, $P_R$ promoter and $P_L$ promoter of the lamda phage, and so forth are known as strong promoters. The gltA gene, the ppc gene and the gdhA gene which have had their respective promoters replaced are then cloned into a plasmid and introduced into the host microorganism, or introduced into the chromosomal DNA of the host microorganism using repetitive DNA, inverted repeat, transposon, or the like.

The activity of CS, PEPC, or GDH can also be increased by replacing the promoter of the gltA gene, the ppc gene, or the gdhA gene on the chromosome with a stronger promoter (see WO87/03006 and Japanese Patent Application Laid-open No. 61-268183), or inserting a strong promoter upstream of the gene coding sequence (see Gene, 29, pp. 231-241 (1984)). Specifically, homologous recombination can be performed between the gltA gene, the ppc gene, or the gdhA gene for which the promoter is replaced with a stronger one or DNA containing a part thereof, and the corresponding gene on the chromosome.

Examples of the enzyme that catalyzes the reaction which branches off from the biosynthetic pathway of the L-glutamic acid and generates a compound other than L-glutamic acid include α-ketoglutarate dehydrogenase (hereinafter, also referred to as "αKGDH"), isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase, and so forth. Of these enzymes, αKGDH is preferred.

In order to decrease or eliminate the activities of the aforementioned enzymes in a microorganism belonging to the genus *Pantoea* or the like, mutations for decreasing or eliminating the intracellular activity of the enzymes can be introduced into the genes of the aforementioned enzymes by a usual mutagenesis treatment method or a genetic engineering method.

Examples of a mutagenesis treatment method include, for example, methods utilizing irradiation with X-rays or ultraviolet rays, methods utilizing treatment with a mutagenesis agent such as N-methyl-N'-nitro-N-nitrosoguanidine, and so forth. The mutation may be introduced into the coding region for the enzyme or a region which regulates expression, such as a promoter.

Examples of the genetic engineering methods include, for example, methods utilizing gene recombination, transduction, cell fusion, and so forth. For example, a drug resistance gene is inserted into a cloned target gene to prepare a gene that has lost its function (defective gene). Subsequently, this defective gene is introduced into a host microorganism, and the target gene on the chromosome is replaced with the aforementioned defective gene by utilizing homologous recombination (gene disruption).

The decrease of intracellular activity of the target enzyme in a cell and the degree of the decrease can be confirmed by measuring the enzyme activity of a cell extract or a purified fraction thereof obtained from a candidate strain and comparing it with that of a wild-type strain. For example, the αKGDH activity can be measured by the method of Reed et al. (Reed L. J. and Mukherjee B. B., Methods in Enzymology, 13, pp. 55-61 (1969)).

Depending on the target enzyme, a target mutant strain can be selected based on the phenotype of the mutant strain. For example, a mutant strain wherein the αKGDH activity is eliminated or decreased cannot proliferate or shows a markedly reduced proliferation rate in a minimal medium containing glucose or a minimal medium containing acetic acid or L-glutamic acid as the sole carbon source under aerobic culture conditions. However, normal proliferation occurs even under the same conditions by adding succinic acid or lysine, methionine, and diaminopimelic acid to a minimal medium containing glucose. By utilizing these phenomena as indicators, a mutant strain with decreased αKGDH activity or which is deficient in the activity can be selected.

A method for preparing an αKGDH gene-deficient strain of *Brevibacterium lactofermentum* by utilizing homologous recombination is described in detail in WO95/34672. Similar methods can be applied to other microorganisms.

Furthermore, techniques such as the cloning of genes and digestion and ligation of DNA, transformation, and so forth are described in detail in Molecular Cloning, 2nd Edition, Cold Spring Harbor Press (1989), and so forth.

A specific example of a mutant strain deficient in αKGDH activity or with decreased αKGDH activity obtained as described above includes *Pantoea ananatis* AJ13356. *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary) on Feb. 19, 1998 and received an accession number of FERM P-16645. It was then converted to an international deposit under the provisions of Budapest Treaty on Jan. 11, 1999 and received an accession number of FERM BP-6615. The *Pantoea ananatis* AJ13356 is deficient in αKGDH activity as a result of disruption of the αKGDH-E1 subunit gene (sucA).

When *Pantoea ananatis*, which is an example of the microorganism used in the present invention, is cultured in a medium containing a saccharide, mucus is extracellularly secreted, occasionally resulting in low operation efficiency. Therefore, when *Pantoea ananatis* which secretes mucus is used, it is preferable to use a mutant strain that secretes less mucus as compared with a wild-type strain. Examples of mutagenesis treatment include, for example, methods utilizing irradiation with X-ray or ultraviolet ray, methods utilizing treatment with a mutagenesis agent such as N-methyl-N'-nitro-N-nitrosoguanidine, and so forth. A mutant strain with decreased secretion of mucus can be selected by inoculating mutagenized bacterial cells in a medium containing a saccharide, for example, an LB medium plate containing 5 g/L of glucose, culturing them while tilting the plate about 45 degrees and selecting a colony that does not show a flow of mucus.

In the present invention, the impartation or enhancement of L-glutamic acid-producing ability and the impartation of other desirable properties such as reducing mucus secretion as described above can be carried out in any order.

The nucleotide sequence of the sucA gene of *Pantoea ananatis* as a gene used for the breeding of such L-glutamic acid-producing bacteria as described above and the amino acid sequence of the αKGDH-E1 subunit encoded by the gene are shown SEQ ID NO: 1 and SEQ ID NO: 3.

Furthermore, the nucleotide sequence of the plasmid RSFCPG containing the gltA gene, gdhA gene, and ppc gene derived from *Escherichia coli* (see Reference Example 1) is shown in SEQ ID NO: 8. In SEQ ID NO: 8, the coding regions of the gltA gene, gdhA gene, and ppc gene are shown at nucleotide numbers 1770 to 487 (encoded by the complementary strand), 2598 to 3941, and 7869 to 5218 (encoded by the complementary strand), respectively. The amino acid sequences of CS, GDH, and PEPC encoded by these genes are shown in SEQ ID NOS: 9, 10, and 11, respectively. Furthermore, the nucleotide sequence of plasmid pSTVCB containing the gltA gene derived from *Brevibacterium lactofermentum* (see Reference Example 1) and the amino acid sequence of CS encoded by this gene are shown in SEQ ID NO: 12 and SEQ ID NO: 13, respectively.

CS, GDH, and PEPC may include, besides the wild-type sequences, sequences which have substitution, deletion, insertion, addition, or inversion of one or several amino acid residues that do not substantially degrade the activities of the enzymes. Although the number of "several" amino acid residues referred to herein differs depending on positions in the three-dimensional structures of the proteins or types of amino acid residues, it may be specifically between 2 to 30, preferably between 2 to 20, more preferably between 2 to 10. Therefore, changes to CS, GDH, or PEPC such as those described above are typically conservative changes so as to maintain the activity of CS, GDH, or PEPC. Substitution changes include those in which at least one residue in the amino acid sequence has been removed and a different residue inserted in its place. Examples of amino acids which may be substituted for an original amino acid in a CS, GDH, or PEPC protein and which are regarded as conservative substitutions include: Ala substituted with ser or thr; arg substituted with gln, his, or lys; asn substituted with glu, gln, lys, his, or asp; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, or tyr; ile substituted with leu, met, val, or phe; leu substituted with ile, met, val, or phe; lys substituted with asn, glu, gln, his, or arg; met substituted with ile, leu, val, or phe; phe substituted with trp, tyr, met, ile, or leu; ser substituted with thr or ala; thr substituted with ser or ala; trp substituted with phe or tyr; tyr substituted with his, phe, or trp; and val substituted with met, ile, or leu.

Examples of DNA coding for substantially the same protein or peptide as CS, GDH, or PEPC include DNA hybridizable with an open reading frame (ORF) of the nucleotide sequence shown in SEQ ID NO: 12 or SEQ ID NO: 8, or a probe that can be prepared from the nucleotide sequence under stringent conditions and encodes a protein having the activity of CS, GDH, or PEPC. The "stringent conditions" referred to herein include conditions under which so-called specific hybrid is formed, and non-specific hybrid is not formed. It is difficult to clearly express this condition by using any numerical value. However, for example, stringent conditions may include conditions under which DNAs having high homology, for example, DNAs having homology of not less than 50%, preferably not less than 70%, more preferably not less than 90%, most preferably not less than 95% hybridize with each other, but DNAs having homology lower than the above do not hybridize with each other. Alternatively, stringent conditions include conditions whereby DNAs hybridize with each other at a salt concentration typically used during washing in Southern hybridization, i.e., 1×SSC, 0.1% SDS, preferably 0.1×SSC, 0.1% SDS, at 60° C.

The ORF of the nucleotide sequence of SEQ ID NO: 12 or SEQ ID NO: 8 or a partial sequence thereof can also be used as the probe. Such a probe can be prepared by PCR using oligonucleotides based on the nucleotide sequence of SEQ ID NO: 8 or 12 as primers and a DNA fragment containing the nucleotide sequence of SEQ ID NO: 8 or 12 or a partial nucleotide sequence thereof as a template. When a DNA fragment having a length of about 300 bp is used as the probe, the washing conditions for the hybridization can be, for example, 2×SSC and 0.1% SDS at 50° C.

It is sufficient that the deletion-type sucA gene used for gene disruption has homology to such a degree that it causes homologous recombination with the sucA gene on a chromosomal DNA of an objective microorganism. Such homology is preferably not less than 85%, more preferably not less than 90%, particularly preferably not less than 95%. Moreover, DNAs hybridizable under stringent conditions may cause homologous recombination.

Specific examples of such a strain obtained as described above include the AJ13601 strain derived from the aforementioned *Pantoea ananatis* AJ13355 strain. This strain was obtained by selecting a low mucus-producing strain from the AJ13355 strain, disrupting the αKGDH gene, introducing the gltA, ppc, and gdhA genes derived from *Escherichia coli*, and the gltA gene derived from *Brevibacterium lactofermentum*, selecting a strain which is resistant to L-glutamic acid at high concentration and low pH, and selecting a strain which shows superior growth and L-glutamic acid-producing ability.

By culturing the L-glutamic acid-accumulating microorganism in a liquid medium that is adjusted to a pH that allows precipitation of L-glutamic acid, L-glutamic acid can be produced and accumulated while it is precipitated. The "conditions that allow precipitation of L-glutamic acid produced by the microorganism" referred to herein means conditions that allow precipitation of L-glutamic acid when the L-glutamic acid-accumulating microorganism produces and accumulates L-glutamic acid. Although the pH of these conditions may vary depending on the L-glutamic acid-producing ability of the microorganism, it is usually 3 to 5, preferably 4.5 or less, more preferably 4 or less when the microorganism is a bacterium belonging to the genus *Pantoea*.

Furthermore, as for the aforementioned pH condition that allows precipitation of L-glutamic acid, the pH is determined on conditions which allow the L-glutamic acid-accumulating microorganism to metabolize a carbon source in a liquid medium containing L-glutamic acid at a saturation concentration, and exhibit an ability to cause accumulation of L-glutamic acid in the medium in an amount which exceeds the saturation concentration of L-glutamic acid in the medium at that pH.

When the L-glutamic acid-accumulating microorganism is cultured in a medium under the aforementioned conditions, the amount of L-glutamic acid which accumulates can be increased by adding pantothenic acid to the medium. This is presumably because the secondary production of acetoin and 2,3-butanediol is reduced by the addition of pantothenic acid in the medium, and as a result, the fermentation yield of L-glutamic acid is improved.

The pantothenic acid to be contained in the medium is preferably added as a pantothenic acid salt. The amount of the pantothenic acid salt is preferably 1 mg/L or more, more preferably 4 mg/L or more, particularly preferably 8 mg/L or more. The type of pantothenic acid salt is not particularly limited, and examples include calcium salt, sodium salt, and so forth.

Pantothenic acid may be present in the medium during the whole culture process, or only during part of the process. For example, when the method of the present invention comprises the step of proliferating the L-glutamic acid accumulating microorganism and the step of allowing production of L-glutamic acid, pantothenic acid may be present in the medium during at least the step of allowing production of L-glutamic acid, and pantothenic acid may or may not be contained in the medium during the step of proliferating the L-glutamic acid-accumulating microorganism. Furthermore, as for the step of allowing production of L-glutamic acid, the amount of pantothenic acid may not necessarily be within the aforementioned range during the entire time period of this step. That is, pantothenic acid may be present so that the amount is within the aforementioned range during an early part of the step, and the amount may be reduced as the culture progresses. Additional pantothenic acid may also be added intermittently.

Known methods of producing L-glutamic acid using an L-glutamic acid-accumulating microorganism while precipitating L-glutamic acid can be used, except that a medium containing pantothenic acid is used (for example, JP 2001-333769 A (EP 1078989 A), JP 2002-238591 A (EP 1233070 A), JP 2002-238592 A (EP 1233068 A), JP 2002-238593 A (EP 1233069 A)).

For example, one of the preferred embodiments of the method of the present invention is to produce L-glutamic acid by culturing an L-glutamic acid-accumulating microorganism in a medium containing a pantothenic acid salt and having a pH of 5.0 or less, and in which the total content of organic acids that inhibit growth of the microorganism is an amount that does not inhibit the growth of the microorganism (see Japanese Patent Laid-open No. 2002-238591 A (European Patent Laid-open No. 1233070)). In this embodiment, the organic acid that inhibits growth of a microorganism at a pH of a medium means an organic acid that has an inhibitory effect on the growth of the microorganism when it exists at a certain concentration (usually 0.5 g/L or more) in the medium at the pH, and it is usually an organic acid having 1-3 carbons, i.e., formic acid, acetic acid, or propionic acid.

The total content of the organic acid is preferably 0.4 g/L or less, more preferably 0.3 g/L or less, even more preferably 0.2 g/L or less.

Another preferred embodiment of the method of the present invention is to produce an L-glutamic acid which includes culturing an L-glutamic acid-accumulating microorganism at a first pH optimal for growth of the microorganism and then culturing the microorganism at a second pH optimal for production of L-glutamic acid by the microorganism and lower than the first pH, and in which the L-glutamic acid-accumulating bacterium is cultured in a medium containing pantothenic acid during at least the culture at the second pH (see Japanese Patent Laid-open No. 2002-238592 (European Patent Laid-open No. 1233068)).

Another preferred embodiment of the method of the present invention is to produce an L-glutamic acid which includes culturing an L-glutamic acid-accumulating microorganism at a first pH at which growth of the microorganism is not inhibited by organic acids contained in the medium, and then culturing the microorganism at a second pH which is optimal for production of L-glutamic acid by the microorganism and which is lower than the first pH, and wherein the L-glutamic acid-accumulating bacterium is cultured in the medium containing pantothenic acid during at least the culture at the second pH (see Japanese Patent Laid-open No. 2002-238591 (European Patent Laid-open No. 1233070)).

It was found that an L-glutamic acid-producing bacterium was generally inhibited by an organic acid under acidic conditions, whereas it could consume an organic acid under neutral conditions (see Japanese Patent Laid-open No. 2002-238591 (European Patent Laid-open No. 1233070)). Based on this property, by growing the cells at a neutral pH and then changing the pH to be acidic to produce L-glutamic acid, it becomes possible to obtain higher productivity and it also becomes possible to use various materials as a sugar source.

In this embodiment, the "organic acid" means an organic acid that has an inhibitory effect on the growth of the microorganism when it exists at a certain concentration (usually 0.5 g/L or more) in a medium at the second pH, and the organic acid usually has 1-3 carbons, i.e., formic acid, acetic acid, or propionic acid.

The first pH and the second pH are selected so that they meet the properties of the chosen L-glutamic acid-producing bacterium. These pH values can easily be measured by those skilled in the art. For example, the pH at which inhibition of growth of a microorganism is not caused by an organic acid in a medium can be determined by culturing an L-glutamic acid-producing bacterium in a medium containing an organic acid adjusted to various pH values, measuring cell amounts based on absorbance or the like, and comparing the cell amounts with cell amounts of the L-glutamic acid-producing bacterium cultured under the same conditions but in the absence of the organic acid. The pH which is suitable for the production of L-glutamic acid refers to the pH at which L-glutamic acid accumulates in a medium, which is determined by culturing an L-glutamic acid-producing bacterium in media at various pH values. Specifically, it can be determined by measuring amounts of L-glutamic acid which has accumulated in media at various pH values and comparing them.

The first pH is not particularly limited so long as growth of the microorganism is not inhibited by the organic acid in the medium, and it is usually 5.0 to 8.0.

The second pH is preferably a pH at which the produced L-glutamic acid precipitates, and such pH is usually 3.0 to 5.0. Reducing productivity by the accumulation of L-glutamic acid at a high concentration can be obviated by performing the culture at the pH at which the produced L-glutamic acid precipitates.

The first pH and the second pH may not be strictly constant during the culture so long as the advantage of the present invention can be obtained, and they may fluctuate.

The L-glutamic acid-producing bacterium produces L-glutamic acid even at the first pH, and therefore pH is lowered by the produced L-glutamic acid. Therefore, the culture at the first pH is preferably performed while maintaining pH of the medium at the first pH by adding an alkalizing substance to the medium.

Although the alkalizing substance is not particularly limited so long as it does not adversely affect the growth of the L-glutamic acid-producing bacterium or L-glutamic acid production, ammonia gas is preferred.

The pH of the medium may be lowered from the first pH to the second pH by adding an acidic substance. However, pH is lowered by production of L-glutamic acid by the L-glutamic acid-producing bacterium during the culture as described above. Therefore, it is preferable to lower the pH of the medium from the first pH to the second pH by controlling the amount of alkalizing substance which is added, because the addition of the acidic substance can be omitted.

The culture at the first pH may be continued until the organic acid in the medium is depleted. "Depletion" means that the amount of the organic acid decreases to a level at which growth of the L-glutamic acid-producing bacterium is not inhibited during the culture at the second pH. Such a level of the organic acid can be easily measured by those skilled in the art. For example, the level can be determined by culturing an L-glutamic acid-producing bacterium in media containing an organic acid at various concentrations at the second pH, measuring cell amounts of the L-glutamic acid-producing bacterium, and comparing the cell amounts with cell amounts of the L-glutamic acid-producing bacterium cultured under the same conditions but in the absence of the organic acid. Generally, as the second pH becomes lower, the level of the organic acid also becomes lower.

A further preferred embodiment of the method of the present invention is to produce L-glutamic acid by fermentation by culturing an L-glutamic acid-accumulating bacterium in a medium whereby the pH is controlled so that L-glutamic acid which is produced is precipitated to cause accumulation of L-glutamic acid in the medium while precipitating the L-glutamic acid, wherein crystals of L-glutamic acid are induced to exist in the medium during a period wherein the L-glutamic acid concentration in the medium is lower than the concentration at which natural crystallization of L-glutamic acid occurs, and the medium contains pantothenic acid (see Japanese Patent Laid-open No. 2002-238593 (European Patent Laid-open No. 1233069)). The "natural crystallization" means that, when a microorganism having an ability to produce L-glutamic acid accumulates L-glutamic acid, the L-glutamic acid concentration in the medium exceeds the saturation concentration of L-glutamic acid, and thus L-glutamic acid naturally precipitates in the medium.

To make crystals of L-glutamic acid exist in the medium means artificially providing the crystals of L-glutamic acid in the medium. Examples of include adding crystals, dissolving a certain amount of L-glutamic acid in the medium at the start of the culture, and decreasing the pH during the culture to forcibly precipitate crystals, and so forth. The amount of crystals made to exist in the medium is usually 0.01 to 10 g/L. Furthermore, the period where the crystals are made to exist is preferably a period where the amount of accumulated L-glutamic acid in the medium increases to a concentration around the saturation concentration (for example, when pH is 4.5 or higher, 25 g/L or more). The amount of L-glutamic acid crystals that exist in the medium and the concentration of L-glutamic acid can be measured by methods well known to those skilled in the art. Crystals of L-glutamic acid are measured after the medium is left standing, and the crystals are collected by decantation. The concentration of L-glutamic acid in the medium is a concentration of dissolved L-glutamic acid. When crystals precipitate in the medium, the concentration of L-glutamic acid means the L-glutamic acid concentration which is measured in a clear solution obtained by separating solid content from the medium by centrifugation (or filtration).

Making the crystals of L-glutamic acid exist in the medium is preferably done by the addition of the crystals of L-glutamic acid.

Crystals of L-glutamic acid include those of α-form and β-form (H. Takahashi, T. Takenishi, N. Nagashima, Bull. Chem. Soc. Japan, 35, 923 (1962); J. D. Bernal, Z. Krist., 78, 363 (1931); S. Hirokawa, Acta Cryst., 8, 637 (1955)). When crystals of the α-form are to be obtained, the crystals to be added are preferably those of the α-form.

The preferred amount of crystals to be added varies depending on the conditions, including the form of the crystals and so forth, and it is usually 0.2 g/L or more for the α-form crystals. If the crystals are added in the aforementioned amount or a larger amount, α-form crystals can be obtained with good reproducibility. Crystals of α-form can be handled more easily than compared with crystals of the β-form in view of the morphology thereof.

As the medium used for the present invention, a usual nutrient medium containing a carbon source, nitrogen source, and inorganic salts as well as organic trace amount nutrients such as amino acids and vitamins as required can be used, except that it contains pantothenic acid, and the pH is adjusted to satisfy the predetermined conditions. Either a synthetic medium or natural medium may be used. Any carbon source and nitrogen source that can be used by the chosen strain may be used in the medium.

Saccharides such as glucose, glycerol, fructose, sucrose, maltose, mannose, galactose, starch hydrolysate, and molasses can be used as the carbon source. In addition, organic acids such as acetic acid and citric acid may be used alone or in combination with another carbon source.

Ammonia, ammonium salts such as ammonium sulfate, ammonium carbonate, ammonium chloride, ammonium phosphate and ammonium acetate, nitrates, and so forth are used as the nitrogen source.

Amino acids, vitamins, fatty acids, nucleic acids, and those containing these substances such as peptone, casamino acid, yeast extract, and soybean protein decomposition products are used as the organic trace nutrients. When an auxotrophic mutant strain that requires an amino acid and so forth for metabolization or growth is used, the required nutrient must be supplemented.

Phosphates, magnesium salts, calcium salts, iron salts, manganese salts, and so forth are used as mineral salts.

As for the culture method, an aeration culture at 20 to 42° C. is usually performed provided that the pH is controlled to be a predetermined value, preferably 3 to 5.

After completion of the culture, the L-glutamic acid which has precipitated in the culture can be collected by centrifugation, filtration, or the like. L-Glutamic acid dissolved in the medium can be also collected by known methods. For example, the L-glutamic acid can be isolated by concentrating the culture broth to crystallize it or isolated by ion exchange chromatography or the like. It is also possible to crystallize L-glutamic acid dissolved in the medium and then collect the crystallized L-glutamic acid along with the L-glutamic acid precipitated during the culture.

When the L-glutamic acid exceeds the saturation concentration and precipitates, the concentration of L-glutamic acid dissolved in the medium is maintained at a constant level.

Therefore, the effect of a high concentration of L-glutamic acid on microorganisms can be reduced. Accordingly, it also becomes possible to breed a microorganism which has even better L-glutamic acid-producing ability. Furthermore, since L-glutamic acid is precipitated as crystals, acidification of the culture broth by accumulation of L-glutamic acid is suppressed, and therefore the amount of alkali which needs to be used for maintaining the pH of the culture can significantly be reduced.

EXAMPLES

Hereafter, the present invention will be more specifically explained with reference to the following non-limited examples.

Reference Example 1

<1> Screening of Microorganism Having L-Glutamic Acid Resistance in Acidic Environment Screening of a microorganism having L-glutamic acid resistance in an acidic environment was performed as follows. One (1) g each of about 500 samples obtained from nature including soil, fruits, plant bodies, river water, and so forth was suspended in 5 mL of sterilized water, and 200 μL thereof was applied on 20 mL of solid medium adjusted to pH 4.0 with HCl. The composition of the medium was as follows: 3 g/L of glucose, 1 g/L of ammonium sulfate, 0.2 g/L of magnesium sulfate heptahydrate, 0.5 g/L of potassium dihydrogenphosphate, 0.2 g/L of sodium chloride, 0.1 g/L of calcium chloride dihydrate, 0.01 g/L of ferrous sulfate heptahydrate, 0.01 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 50 μg/L of biotin, 50 μg/L of calcium pantothenate, 50 μg/L of folic acid, 50 μg/L of inositol, 50 μg/L of niacin, 50 μg/L of p-aminobenzoic acid, 50 μg/L of pyridoxine hydrochloride, 50 μg/L of riboflavin, 50 μg/L of thiamin hydrochloride, 50 mg/L of cycloheximide, and 20 g/L of agar.

The media plated with the above samples were incubated at 28° C., 37° C., or 50° C. for 2 to 4 days, and 378 colony-forming strains were obtained.

Subsequently, each of the strains obtained as described above was inoculated in a test tube of 16.5 cm in length and 14 mm in diameter containing 3 mL of liquid medium (adjusted to pH 4.0 with HCl) which contained L-glutamic acid at a saturation concentration, and cultured at 28° C., 37° C., or 50° C. for 24 hours to 3 days with shaking. Then, the strains which grew were selected. The composition of the aforementioned medium was as follows: 40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, and 2 g/L of yeast extract.

Thus, 78 strains of microorganisms which showed L-glutamic acid resistance in an acidic environment were successfully obtained.

<2> Selection of the Strains Showing a Superior Growth Rate from Microorganisms Having L-Glutamic Acid Resistance in an Acidic Environment The various microorganisms having L-glutamic acid resistance in an acidic environment obtained as described above are each inoculated into a test tube of 16.5 cm in length and 14 mm in diameter containing 3 mL of medium (adjusted to pH 4.0 with HCl) obtained by adding 20 g/L of glutamic acid and 2 g/L of glucose to M9 medium (Sambrook, J., Fritsh, E. F. and Maniatis, T., "Molecular Cloning", Cold Spring Harbor Laboratory Press, U.S.A., 1989), and the turbidity of the medium was measured over time, so to select strains showing a favorable growth rate. As a result, the AJ13355 strain was obtained from soil in Iwata-shi, Shizuoka, Japan which showed a favorable growth rate. This strain was determined to be *Enterobacter agglomerans* based on its bacteriological properties described above. *Enterobacter agglomerans* includes those re-classified into *Pantoea agglomerans, Pantoea ananatis, Pantoea stewartii*, and so forth on the basis of nucleotide sequence analysis of 16S rRNA or the like, and the AJ13355 strain is classified into *Pantoea ananatis* among these.

<3> Acquisition of a Strain with Reduced Mucus Secretion from *Pantoea ananatis* AJ13355 Strain Since the *Pantoea ananatis* AJ13355 strain secretes mucus extracellularly when cultured in a medium containing a saccharide, operation efficiency is not favorable. Therefore, a strain with reduced mucus secretion was obtained by the ultraviolet irradiation method (Miller, J. H. et al., "A Short Course in Bacterial Genetics; Laboratory Manual", p. 150, 1992, Cold Spring Harbor Laboratory Press, U.S.A.).

The *Pantoea ananatis* AJ13355 strain was irradiated with an ultraviolet ray for 2 minutes at a position 60 cm away from a 60-W ultraviolet lamp and cultured in LB medium overnight to fix the mutation. The mutagenized strain was diluted and inoculated in LB medium containing 5 g/L of glucose and 20 g/L of agar so that about 100 colonies per plate emerged, and was cultured at 30° C. overnight while the plate was tilted at about 45 degrees, and then 20 colonies without mucus flow were selected.

As a strain for which no revertant emerged even after subculturing 5 times in LB medium containing 5 g/L of glucose and 20 g/L of agar, and which showed growth equivalent to the parent strain in LB medium, LB medium containing 5 g/L of glucose and M9 medium (Sambrook, J. et al., Molecular Cloning, 2nd Edition, Cold Spring Harbor Press, U.S.A., 1989) supplemented with 20 g/L of L-glutamic acid and 2 g/L of glucose and adjusted to pH 4.5 with HCl, the SC17 strain was selected from the strains selected above.

<4> Construction of Glutamic Acid-Producing Bacterium from *Pantoea ananatis* SC17 Strain (1) Preparation of αKGDH Deficient Strain from *Pantoea ananatis* SC17 Strain A strain that was deficient in αKGDH and had enhanced L-glutamic acid biosynthetic system was prepared from the *Pantoea ananatis* SC17 strain.

(i) Cloning of αKGDH Gene (Hereinafter, Referred to as "sucAB") of *Pantoea Ananatis* AJ13355 Strain The sucAB gene of the *Pantoea ananatis* AJ13355 strain was cloned by selecting a DNA fragment complementing the acetic acid-unassimilating property of the αKGDH-E1 subunit gene (hereafter, referred to as "sucA")-deficient strain of *Escherichia coli* from chromosomal DNA of the *Pantoea ananatis* AJ13355 strain.

The chromosomal DNA of the *Pantoea ananatis* AJ13355 strain was isolated by a method usually employed for extracting chromosomal DNA from *Escherichia coli* (Text for Bioengineering Experiments, Edited by the Society for Bioscience and Bioengineering, Japan, pp. 97-98, Baifukan, 1992). The pTWV228 (resistant to ampicillin), which is a commercial product of Takara Shuzo Co., Ltd, and was used as a vector.

The chromosomal DNA of the AJ13355 strain digested with EcoT22I and pTWV228 which had been digested with PstI were ligated using T4 ligase, and the ligation mixture was used to transform the sucA-deficient *Escherichia coli* JRG465 strain (Herbert, J. et al., Mol. Gen. Genetics, 105, 182 (1969)). A strain able to grow in an acetate minimal medium was selected from the transformant strains obtained above, and a plasmid was extracted from the obtained strain and designated pTWVEK101. The *Escherichia coli* JRG465 strain harboring pTWVEK101 recovered auxotrophy for succinic acid or L-lysine and L-methionine, besides the trait of acetic acid-unassimilating property. This suggests that pTWVEK101 contained the sucA gene of *Pantoea ananatis*.

FIG. 1 shows a restriction enzyme map of a DNA fragment derived from *Pantoea ananatis* in pTWVEK101. In the nucleotide sequence of the hatched portion in FIG. 1, nucleotide sequences considered to be two full length ORFs and two nucleotide sequences considered to be partial sequences of ORFs were found. Amino acid sequences which are predicted to be encoded by these ORFs or the partial sequences are shown in SEQ ID NOS:2-5 starting from 5' side. As a result of homology search, portions of the nucleotide sequences were determined to contain a 3' end partial sequence of the succinate dehydrogenase iron-sulfur protein gene (sdhB), full length sucA and αKGDH-E2 subunit gene (sucB), and a 5' end partial sequence of the succinyl CoA synthetase β subunit gene (sucC). A comparison of the amino acid sequences deduced from these nucleotide sequences with those derived from *Escherichia coli* (Eur. J. Biochem., 141, pp. 351-359 (1984); Eur. J. Biochem., 141, pp. 361-374 (1984); Biochemistry, 24, pp. 6245-6252 (1985)) showed that these amino acid sequences are very high homologus to each other. In addition, it was found that a cluster of sdhB-sucA-sucB-sucC was located on the chromosome of *Pantoea ananatis*, as in *Escherichia coli* (Eur. J. Biochem., 141, pp. 351-359 (1984); Eur. J. Biochem., 141, pp. 361-374 (1984); Biochemistry, 24, pp. 6245-6252 (1985)).

(ii) Acquisition of αKGDH-Deficient Strain Derived from *Pantoea ananatis* SC17 Strain The homologous recombination was performed using the sucAB gene of *Pantoea ananatis* obtained as described above to obtain an αKGDH-deficient strain of *Pantoea ananatis*.

After pTWVEK101 was digested with SphI to excise a fragment containing sucA, the fragment was blunt-ended with Klenow fragment (Takara Shuzo Co., Ltd.) and ligated with pBR322 which had been digested with EcoRI and blunt-ended with Klenow fragment, by using T4 DNA ligase (Takara Shuzo Co., Ltd.). The obtained plasmid was digested at the restriction enzyme BglII recognition site, located approximately at the center of sucA by using the enzyme, blunt-ended with Klenow fragment, and then ligated again by using T4 DNA ligase. It was thought that the sucA gene was unable to function due to the introduction of a frameshift mutation into sucA on the newly constructed plasmid during the above procedure.

The plasmid constructed as described above was digested with a restriction enzyme ApaLI, and subjected to agarose gel electrophoresis to recover a DNA fragment containing sucA into which the frameshift mutation was introduced and a tetracycline resistance gene derived from pBR322. The recovered DNA fragment was ligated again using T4 DNA ligase to construct a plasmid for disrupting the αKGDH gene.

The plasmid for disrupting the αKGDH gene obtained as described above was used to transform the *Pantoea ananatis* SC17 strain by electroporation (Miller, J. H., "A Short Course in Bacterial Genetics; Handbook", p. 279, Cold Spring Harbor Laboratory Press, U.S.A., 1992), and a strain wherein sucA on the chromosome was replaced with a mutant sucA of the plasmid by homologous recombination was obtained using the tetracycline resistance as a marker. This strain was designated SC17sucA.

In order to confirm that the SC17sucA strain was deficient in αKGDH activity, the enzyme activity was measured by the method of Reed et al. (Reed, L. J. and Mukherjee, B. B., Methods in Enzymology, 13, pp. 55-61, (1969)) using cells of the strain cultured in LB medium to the logarithmic growth phase. As a result, αKGDH activity of 0.073 (ΔABS/min/mg protein) was detected from the SC17 strain, whereas no αKGDH activity was detected from the SC17sucA strain, and thus it was confirmed that the sucA was eliminated as intended.

(2) Enhancement of L-Glutamic Acid Biosynthesis System of *Pantoea ananatis* SC17sucA Strain Subsequently, the citrate synthase gene, phosphoenolpyruvate carboxylase gene and glutamate dehydrogenase gene derived from *Escherichia coli* were introduced into the SC17sucA strain.

(i) Preparation of a Plasmid Having the gltA Gene, ppc Gene, and gdhA Gene, all Derived from *Escherichia coli*

Figure 2:
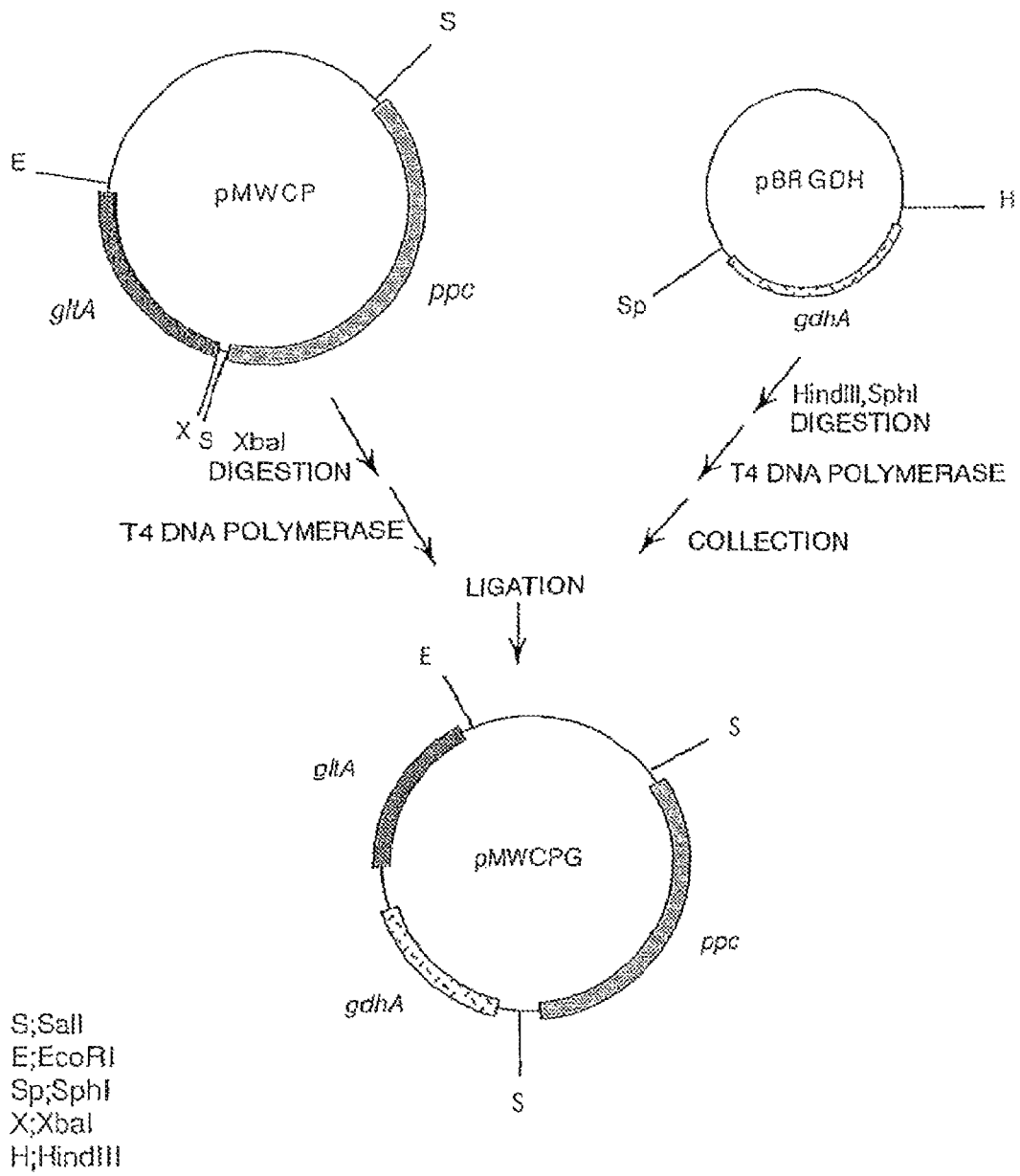
FIG. 2 shows construction of a plasmid pMWCPG containing genes gltA, ppc and gdhA.
Figure 3:
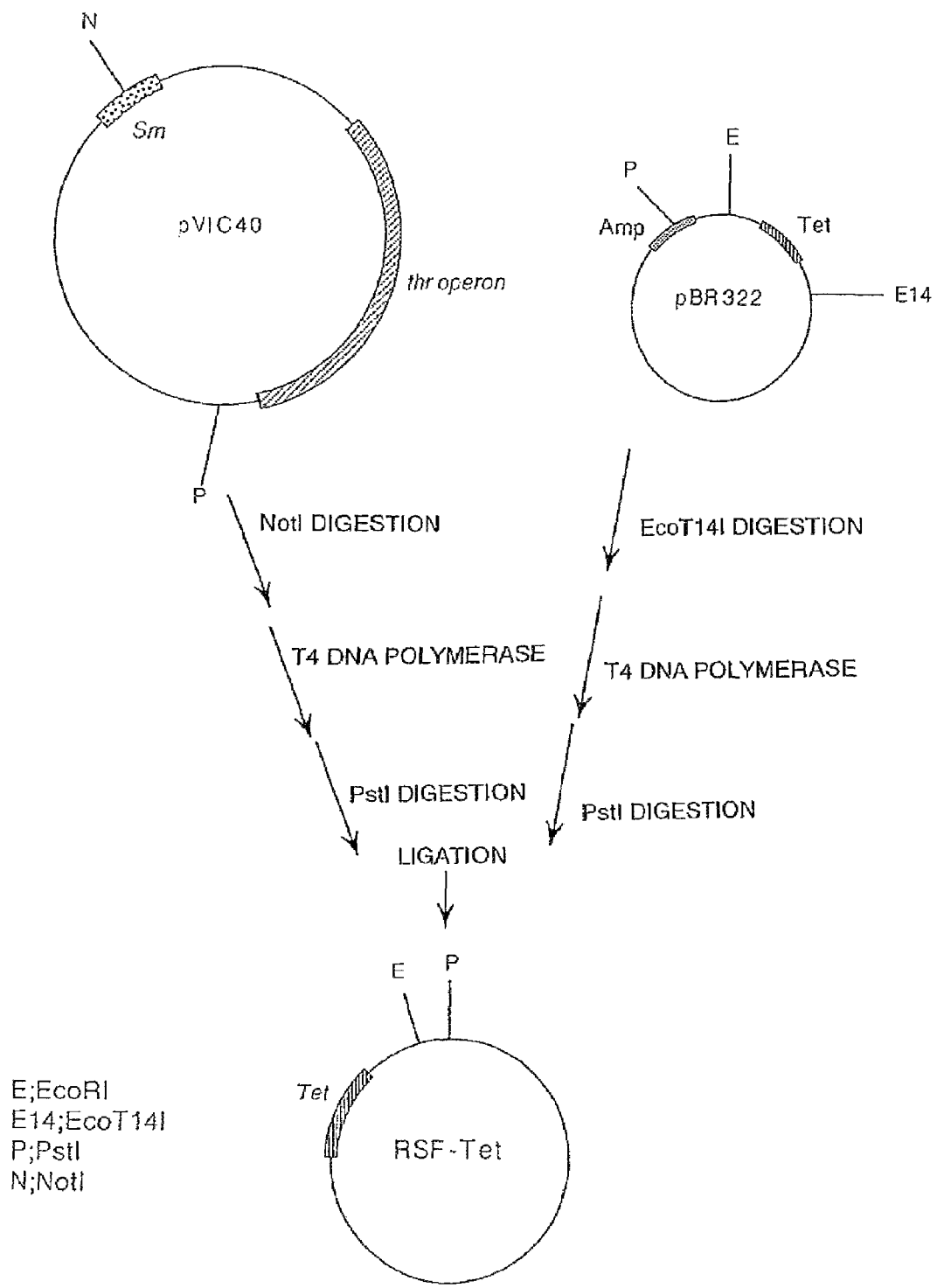
FIG. 3 shows construction of a plasmid RSF-Tet containing the replication origin of the wide host range plasmid RSF1010 and tetracycline resistance gene.

The procedures for preparing a plasmid having the gltA gene, the ppc gene, and the gdhA gene will be explained by referring to FIGS. 2 and 3.

A plasmid having the gdhA gene derived from *Escherichia coli*, pBRGDH (JP 7-203980 A), was digested with HindIII and SphI, and both ends were blunt-ended by treating with T4 DNA polymerase, and then the DNA fragment having the gdhA gene was purified and recovered. Separately, a plasmid having the gltA gene and ppc gene derived from *Escherichia coli*, pMWCP (WO97/08294), was digested with XbaI, and then both ends were blunt-ended with T4 DNA polymerase. This was mixed with the above purified DNA fragment having the gdhA gene and ligated using T4 ligase to obtain the plasmid pMWCPG, which is pMWCP with the addition of the gdhA gene (FIG. 2).

Concurrently, the plasmid pVIC40 (Japanese Patent Laid-open No. 8-047397) having the replication origin of the wide-host-range plasmid RSF1010 was digested with NotI, treated with T4 DNA polymerase, and digested with PstI. pBR322 was digested with EcoT14I, treated with T4 DNA polymerase and digested with PstI. Both products were mixed and ligated using T4 ligase to obtain a plasmid RSF-Tet having the replication origin of RSF1010 and the tetracycline resistance gene (FIG. 3).

Figure 4:
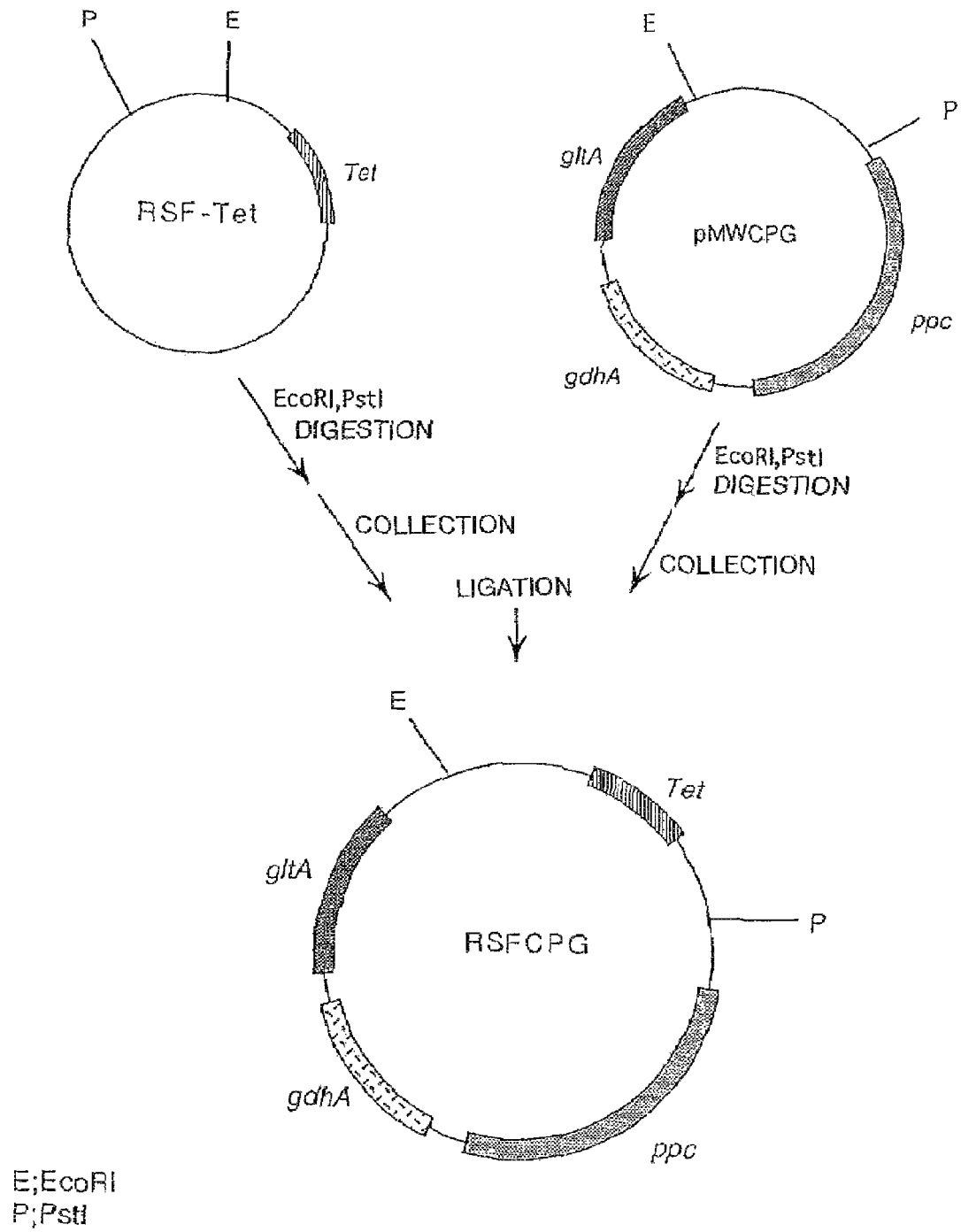
FIG. 4 shows construction of a plasmid RSFCPG containing the replication origin of the wide host range plasmid RSF1010, tetracycline resistance gene, gltA gene, ppc gene and gdhA gene.

Subsequently, pMWCPG was digested with EcoRI and PstI, and a DNA fragment having the gltA gene, the ppc gene, and the gdhA gene was purified and recovered. RSF-Tet was similarly digested with EcoRI and PstI, and a DNA fragment having the replication origin of RSF1010 was purified and recovered. Both products were mixed and ligated using T4 ligase to obtain a plasmid RSFCPG, which corresponded to RSF-Tet containing the gltA gene, the ppc gene, and the gdhA gene (FIG. 4). It was confirmed that the obtained plasmid RSFCPG expressed the gltA gene, the ppc gene, and the gdhA gene based on the supplementation of the auxotrophy of the gltA gene-, ppc gene-, or gdhA gene-deficient strain derived from *Escherichia coli* and measurement of each enzyme activity.

(ii) Preparation of Plasmid Having gltA Gene Derived from *Brevibacterium lactofermentum*

Figure 5:
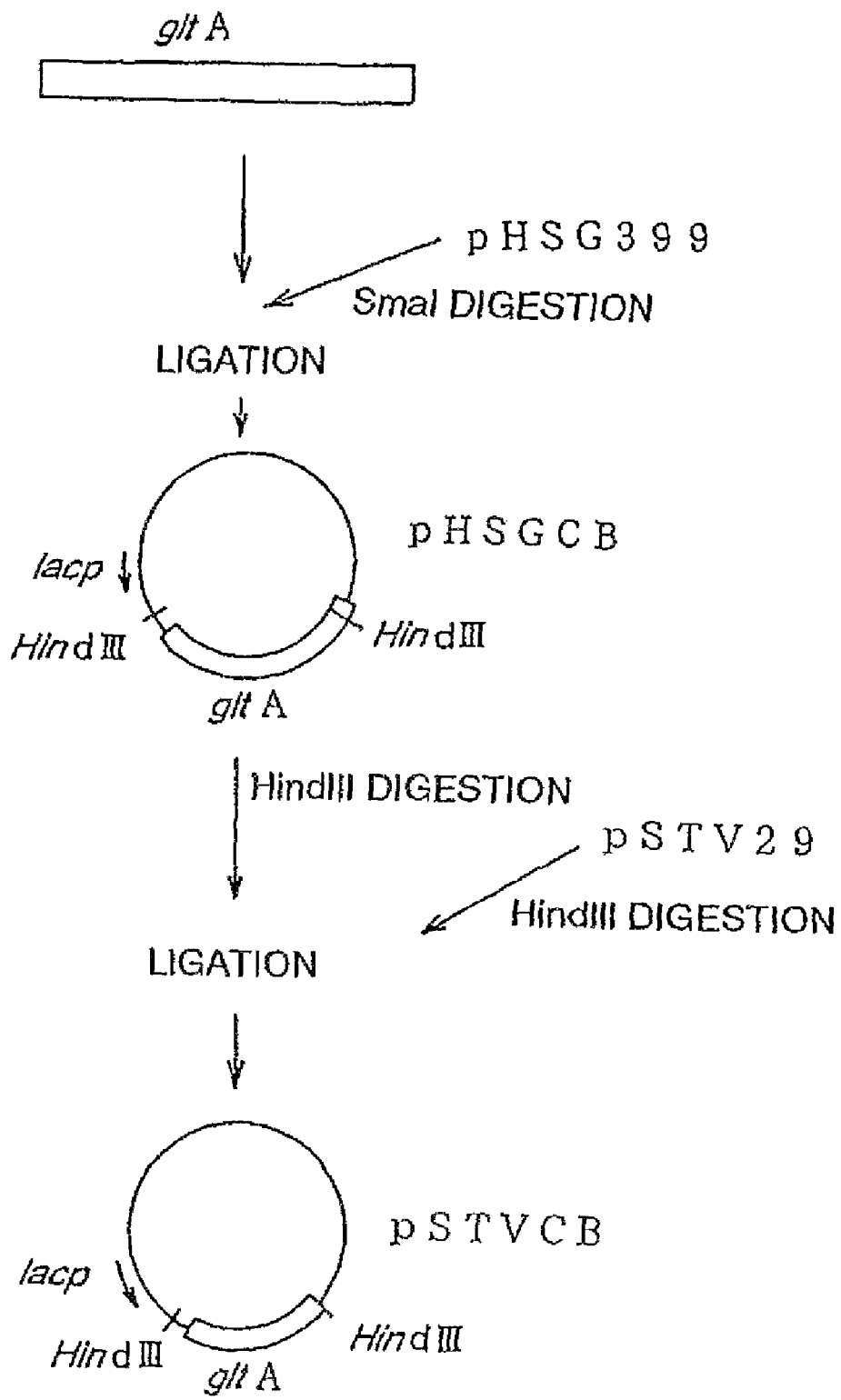
FIG. 5 shows construction of a plasmid pSTVCB containing the gltA gene.

A plasmid having the gltA gene derived from *Brevibacterium lactofermentum* was constructed as follows. PCR was performed using primers having nucleotide sequences SEQ ID NOS:6 and 7 which were prepared based on the nucleotide sequence of the *Corynebacterium* glutamicum gltA gene (Microbiology, 140, pp. 1817-1828 (1994)), and chromosomal DNA of *Brevibacterium lactofermentum* ATCC13869 was used as a template to obtain a gltA gene fragment of about 3 kb. This fragment was inserted into a plasmid pHSG399 (purchased from Takara Shuzo Co., Ltd.) which had been digested with SmaI to obtain a plasmid pHSGCB (FIG. 5). Subsequently, pHSGCB was digested with HindIII, and the excised gltA gene fragment of about 3 kb was inserted into the plasmid pSTV29 (purchased from Takara Shuzo Co., Ltd.) digested with HindIII to obtain a plasmid pSTVCB (FIG. 5). It was confirmed that the obtained plasmid pSTVCB expressed the gltA gene by measuring the enzyme activity in the *Pantoea ananatis* AJ13355 strain.

(iii) Introduction of RSFCPG and pSTVCB into SC17sucA Strain

The *Pantoea ananatis* SC17sucA strain was transformed with RSFCPG by electroporation to obtain a transformant SC17sucA/RSFCPG strain which was resistant to tetracycline. Furthermore, the SC17sucA/RSFCPG strain was transformed with pSTVCB by electroporation to obtain a transformant SC17sucA/RSFCPG+pSTVCB strain showing chloramphenicol resistance.

<4> Acquisition of a Strain with Improved Resistance to L-Glutamic Acid in a Low pH Environment A strain with improved resistance to L-glutamic acid at high concentrations in a low pH environment (hereafter, also referred to as "strain with high-concentration Glu-resistance at low pH") was isolated from the *Pantoea ananatis* SC17sucA/RSFCPG+pSTVCB strain.

The SC17sucA/RSFCPG+pSTVCB strain was cultured overnight at 30° C. in LBG medium (10 g/L of trypton, 5 g/L of yeast extract, 10 g/L of NaCl, 5 g/L of glucose), and the cells washed with saline was appropriately diluted and plated on an M9-E medium (4 g/L of glucose, 17 g/L of $Na_2HPO_4\cdot 12H_2O$, 3 g/L of $KH_2PO_4$, 0.5 g/L of NaCl, 1 g/L of $NH_4Cl$, 10 mM of $MgSO_4$, 10 µM of $CaCl_2$, 50 mg/L of L-lysine, 50 mg/L of L-methionine, 50 mg/L of DL-diaminopimelic acid, 25 mg/L of tetracycline, 25 mg/L of chloramphenicol, 30 g/L of L-glutamic acid, adjusted to pH 4.5 with aqueous ammonia) plate. A colony was obtained which emerged after culture at 32° C. for 2 days as a strain with high-concentration Glu-resistance at low pH.

For the obtained strain, the growth level in M9-E liquid medium was measured and L-glutamic acid-producing ability was tested in a 50-ml volume large test tube containing 5 ml of L-glutamic acid production test medium (40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride, and 25 mg/L of chloramphenicol). A strain that exhibited the best growth level and the same L-glutamic acid-producing ability as that of its parent strain, the SC17/RSFCPG+pSTVCB strain, was designated *Pantoea ananatis* AJ13601. The AJ13601 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Aug. 18, 1999 and received an accession number of FERM P-17516. It was then converted to an international deposit under the provisions of Budapest Treaty on Jul. 6, 2000 and received an accession number of FERM BP-7207.

Example 1

The *Pantoea ananatis* AJ13601 strain was cultured in a medium containing calcium pantothenate (12 mg/L) and also in a medium not containing calcium pantothenate to investigate the production of L-glutamic acid.

Specifically, the culture was performed as follows. Cells of the *Pantoea ananatis* AJ13601 strain cultured at 30° C. for 14 hours in the LBG agar medium (10 g/L of trypton, 5 g/L of yeast extract, 10 g/L of NaCl, 15 g/L of agar) containing 25 mg/L of tetracycline hydrochloride and 25 mg/L of chloramphenicol were scraped from one plate and inoculated into 300 ml of seed culture medium having the following composition and contained in a 1 L-volume jar fermenter, and seed culture was performed under conditions of 34° C. and pH 6.0.

Composition of Seed Culture Medium:

| | |
|---|---|
| Sucrose | 50 g/L |
| $MgSO_4\cdot 7H_2O$ | 0.4 g/L |
| $KH_2PO_4$ | 2.0 g/L |
| Yeast extract | 4.0 g/L |
| $FeSO_4\cdot 7H_2O$ | 0.01 g/L |
| $MnSO_4\cdot 5H_2O$ | 0.01 g/L |
| L-Lysine hydrochloride | 0.4 g/L |
| DL-Methionine | 0.4 g/L |
| ε-Diaminopimelic acid | 0.4 g/L |
| Tetracycline hydrochloride | 25 mg/L |
| Chloramphenicol | 25 mg/L |

The pH was adjusted to 6.0 by adding ammonia gas during the culture. The seed culture was finished when depletion of the saccharide in the medium was observed, and the seed culture medium corresponding to 20% volume of the main culture medium was inoculated to 300 ml of the main culture medium contained in a 1 L-volume jar fermenter to perform the main culture under conditions of 34° C. and pH 4.5. The composition of the main culture medium is shown below.

Composition of Main Culture Medium:

| | |
|---|---|
| Glucose | 50 g/L |
| $(NH_4)_2SO_4$ | 5.0 g/L |
| $MgSO_4\cdot 7H_2O$ | 0.4 g/L |
| $KH_2PO_4$ | 6.0 g/L |
| NaCl | 1.5 g/L |
| $FeSO_4\cdot 7H_2O$ | 0.01 g/L |

-continued

| | |
|---|---|
| $MnSO_4 \cdot 5H_2O$ | 0.01 g/L |
| L-Lysine hydrochloride | 0.8 g/L |
| DL-Methionine | 0.6 g/L |
| DL-α,ε-Diaminopimelic acid | 0.6 g/L |
| Tetracycline hydrochloride | 25 mg/L |
| Chloramphenicol | 25 mg/L |
| Calcium chloride dihydrate | 0.75 g/L |
| Calcium pantothenate | 12 mg/L |
| (added only for the culture with pantothenic acid) | |

The pH was adjusted to 4.5 by adding ammonia gas during the culture. After the saccharide in the medium was consumed and depleted, a 700 g/L of glucose aqueous solution was continuously added (5 ml/hr). When the L-glutamic acid concentration in the culture broth reached 45 g/L, 1.0 g/L of L-glutamic acid crystals were added to the medium as seed crystals to promote precipitation of L-glutamic acid in the culture broth.

After the main culture was performed for 50 hours, a marked amount of L-glutamic acid crystals were precipitated in the jar fermenter. Then, ammonia gas was added to raise pH to 6.0 and thereby dissolve all the L-glutamic acid crystals in the jar fermenter. Then, the amount of the produced L-glutamic acid was measured. The L-glutamic acid concentration was measured by using Automatic enzyme electrode analyzer As210 produced by Asahi Chemical Industry.

As a result, it was found that the L-glutamic acid fermentation yield was significantly improved by the addition of pantothenic acid, as shown in Table 1.

TABLE 1

| | No addition of calcium pantothenate | With addition of calcium pantothenate (12 mg/L) |
|---|---|---|
| L-Glutamic acid fermentation yield (%) | 40.2 | 53.3 |

The cause of the improvement of the L-glutamic acid yield provided by the addition of calcium pantothenate was investigated. As a result, reduction of acetoin, 2,3-butanediol and $CO_2$ production was confirmed (Table 2). The acetoin and 2,3-butanediol concentrations were measured by using a gas chromatography apparatus GC1700 produced by Shimadzu with the following conditions.

Column Used:

DB-210 123-0233 produced by J & W Scientific, column length: 30 m, column diameter: 0.32 mm, film thickness: 5 μm Measurement Conditions:

Temperature of vaporization chamber: 250° C.

Carrier gas: He

Pressure: 85.6 kPa

Total flow rate: 97.2 ml/min

Column flow rate: 0.93 ml/min

Linear velocity: 25.0 cm/sec

Purge flow rate: 3.0 ml/min

Split ratio: 100

Column temperature: 70° C.

Makeup gas: He

Makeup flow rate: 30.0 ml/min $H_2$ flow rate: 47 ml/min

Air flow rate: 400 ml/min

The discharged $CO_2$ amount was measured using an Exhaust oxygen carbon dioxide meter Model EX-1562 produced by ABLE. The produced amounts of acetoin and 2,3-butanediol as well as the produced amount of $CO_2$ calculated from these values are shown in Table 2 (all values are represented in terms of carbon amount). The measured values of $CO_2$ discharged from the culture medium were 26.5% with no pantothenic acid and 27.6% with pantothenic acid.

When calcium pantothenate was added to the medium, the amounts of acetoin, 2,3-butanediol, and $CO_2$ generated in association with the secondary production of the foregoing substances (two moles of $CO_2$ is generated for 1 mole each of acetoin and 2,3-butanediol) were reduced by about 14.3% in terms of the carbon balance compared with when calcium pantothenate was not added. Because this value is substantially equivalent to the difference between the L-glutamic acid fermentation yields obtained with and without addition of calcium pantothenate, i.e., about 13.1%, it is considered that the yield improvement effect provided by the addition of calcium pantothenate was mainly caused by reduction of the secondary production of acetoin and 2,3-butanediol.

TABLE 2

| Secondary product (%, in terms of carbon) | No addition of calcium pantothenate | With addition of calcium pantothenate (12 mg/L) |
|---|---|---|
| Acetoin + $CO_2$ generated in association with production of acetoin | 12.0 | 2.5 |
| Butanediol + $CO_2$ generated in association with production of butanediol | 6.1 | 1.3 |

From the above results, the mechanism of the improvement of L-glutamic acid fermentation yield provided by the addition of pantothenic acid was estimated as follows. That is, it is considered that the L-glutamic acid fermentation yield was improved because insufficiency of coenzyme A (CoA) could be compensated by the addition of pantothenic acid. Pantothenic acid is contained in the structure of CoA in the form of pantetheine, and thus it is one of the constituents of CoA. CoA is used as a coenzyme in the process of converting pyruvic acid into acetyl-CoA in the metabolic pathway. On the other hand, acetoin and 2,3-butanediol are generated from pyruvic acid, and $CO_2$ is discharged in association with the production of acetoin. When pantothenic acid was not added to the medium used for the culture of the L-glutamic acid-producing bacterium, acetoin and 2,3-butanediol accumulated in the medium. Therefore, it is considered that CoA was originally insufficient in the bacterium, and sufficient acetyl-CoA was not produced in the bacterium, which resulted in the secondary production of acetoin and 2,3-butanediol.

Figure 6:
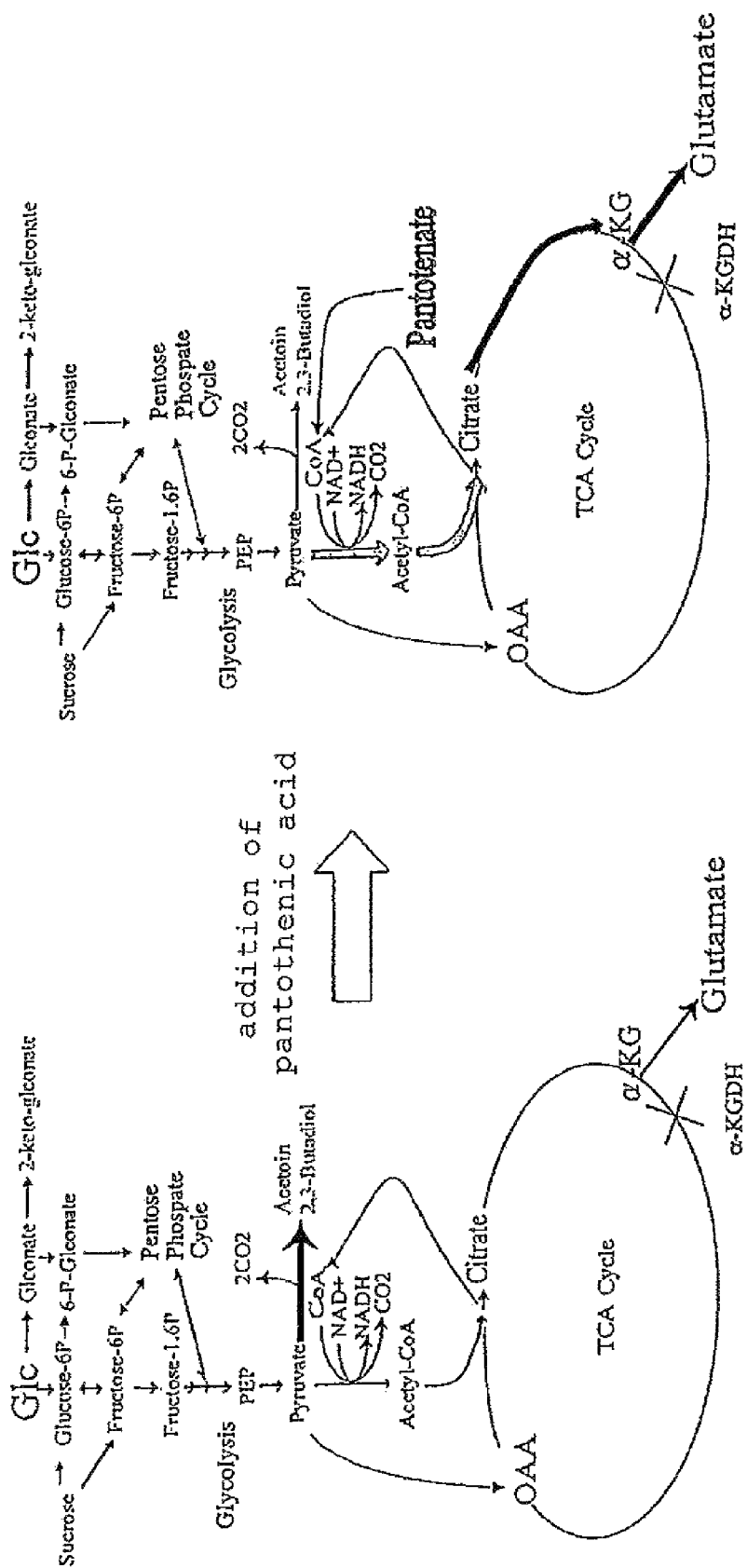
FIG. 6 is an explanatory chart showing the principle of improvement of L-glutamic acid yield provided by addition of pantothenic acid.

On the other hand, when sufficient amounts of CoA was supplied by the addition of pantothenic acid, the reaction caused by the pyruvate dehydrogenase complex (pyruvic acid→acetyl-CoA) was promoted, which reaction had served as a rate-limiting factor due to the insufficiency of CoA, and thus inflow of carbon into the TCA cycle was promoted. Thus, it is considered that the production of L-glutamic acid was promoted via α-ketoglutaric acid (αKG) as a result. Furthermore, when the production of acetoin and 2,3-butanediol decreases, $CO_2$ generated in association with the production of these substances from pyruvic acid also decreases (2 moles of $CO_2$ for 1 mole each of acetoin and 2,3-butanediol). Therefore, it is considered that this reduction also contributed to the improvement of the L-glutamic acid yield (FIG. 6).

On the basis of the above mechanism, it is considered that addition of a substance such as D-panto acid, β-alanine, or D-pantetheine instead of or in addition to the addition of pantothenic acid should provide comparable or more favorable improvement in the yield.

Example 2

Figure 7:
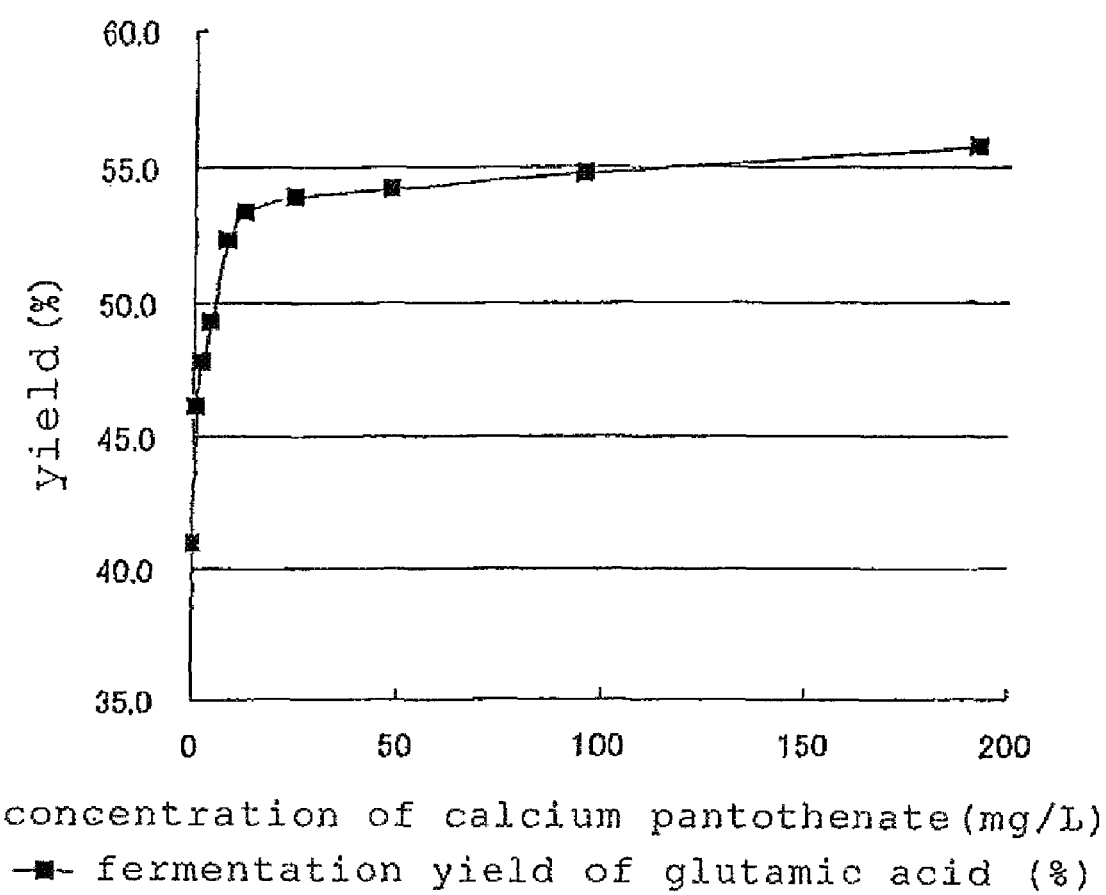
FIG. 7 is a graph showing a relationship between concentrations of calcium pantothenate added to a medium and fermentation yield of L-glutamic acid.

The concentration of calcium pantothenate to be added to the medium was changed to 0 mg/L to 196 mg/L to examine the effect of calcium pantothenate concentration on the L-glutamic acid fermentation yield. The culture was performed in the same manner as in Example 1 except that the calcium pantothenate concentration was changed to 0, 1, 2, 4, 8, 12, 24, 48, 96, or 192 mg/L. The results are shown in FIG. 7. As confirmed from these results, the L-glutamic acid fermentation yield was positively improved depending on the calcium pantothenate concentration. Even when 1 mg/L of calcium pantothenate was added, the yield was improved by about 5% compared with no addition (0 mg/L). Because the yield improvement effect could be obtained depending on the addition concentration until the added calcium pantothenate concentration reached 12 mg/L, it is considered that the yield improvement effect can be obtained even with a concentration lower than 1 mg/L.

Example 3

The main culture was performed with addition of sodium pantothenate instead of calcium pantothenate. The culture conditions were the same as those used in Example 1. Sodium pantothenate was added at a concentration of 12.15 mg/L so that the molar concentration of pantothenic acid is equivalent to that obtained with the addition of 12 mg/L of calcium pantothenate. The results are shown in Table 3.

As shown by the results, equivalent L-glutamic acid fermentation yields were obtained with calcium pantothenate and sodium pantothenate. Thus, it was clarified that the factor of the yield improvement should be pantothenic acid itself, not the counter ion of pantothenic acid.

TABLE 3

|  | Addition of calcium pantothenate (12 mg/L) | Addition of sodium pantothenate (12.15 mg/L) |
| --- | --- | --- |
| L-Glutamic acid fermentation yield (%) | 52.8 | 52.5 |

INDUSTRIAL APPLICABILITY

According to the present invention, L-glutamic acid can be more efficiently produced compared with conventional techniques by using a bacterium such as a bacterium belonging to the genus *Pantoea*.

While the invention has been described with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing L-glutamic acid comprising:
   a) culturing a microorganism belonging to the genus *Pantoea* in a medium which contains pantothenic acid, wherein the pH of the medium is controlled to be 3 to 5 so to induce precipitation of L-glutamic acid, and
   b) collecting said L-glutamic acid from said medium.

2. The method according to claim 1, wherein said microorganism is able to metabolize a carbon source in a second medium which contains L-glutamic acid at a saturation concentration and has the ability to cause accumulation of L-glutamic acid in said second medium, wherein said second medium is at pH 4.0 to 5.0.

3. The method according to claim 1, wherein the microorganism is *Pantoea ananatis*.

4. The method according to claim 2, wherein the microorganism is *Pantoea ananatis*.

5. The method according to claim 1, wherein said pantothenic acid is a pantothenic acid salt, and the concentration of said salt is at least 1 mg/L.

6. The method according to claim 2, wherein said pantothenic acid is a pantothenic acid salt, and the concentration of said salt is at least 1 mg/L.

7. The method according to claim 3, wherein said pantothenic acid is a pantothenic acid salt, and the concentration of said salt is at least 1 mg/L.

8. The method according to claim 4, wherein said pantothenic acid is a pantothenic acid salt, and the concentration of said salt is at least 1 mg/L.

9. The method according to claim 5, wherein said concentration of said salt is 4 mg/L or more.

10. The method according to claim 5, wherein said concentration of said salt is 8 mg/L or more.

11. The method according to claim 6, wherein said concentration of said salt is 4 mg/L or more.

12. The method according to claim 6, wherein said concentration of said salt is 8 mg/L or more.

13. The method according to claim 7, wherein said concentration of said salt is 4 mg/L or more.

14. The method according to claim 7, wherein said concentration of said salt is 8 mg/L or more.

15. The method according to claim 8, wherein said concentration of said salt is 4 mg/L or more.

16. The method according to claim 8, wherein said concentration of said salt is 8 mg/L or more.

* * * * *

SEQUENCE LISTING

```
<160> NUMBER OF SEQ ID NOS: 13

<210> SEQ ID NO 1
<211> LENGTH: 4556
<212> TYPE: DNA
<213> ORGANISM: Pantoea ananatis
<220> FEATURE:
<221> NAME/KEY: CDS
<222> LOCATION: (2)..(121)
<220> FEATURE:
<221> NAME/KEY: CDS
<222> LOCATION: (322)..(3129)
<220> FEATURE:
<221> NAME/KEY: CDS
<222> LOCATION: (3145)..(4368)
<220> FEATURE:
<221> NAME/KEY: CDS
<222> LOCATION: (4437)..(4556)

<400> SEQUENCE: 1 t gca ttc agc gtt ttc cgc tgt cac agc atc atg aac tgt gta agt gtt      49
  Ala Phe Ser Val Phe Arg Cys His Ser Ile Met Asn Cys Val Ser Val
   1               5                  10                  15 tgt cct aaa ggg cta aac ccg acg cgc gct atc ggc cac att aag tcg        97
Cys Pro Lys Gly Leu Asn Pro Thr Arg Ala Ile Gly His Ile Lys Ser
             20                  25                  30 atg ctg ctg caa cgc agc gcg tagttatacc accgggaacc tcaggttccc          148
Met Leu Leu Gln Arg Ser Ala
         35 ggtattttac ggaagcctct gtaaacgcgg tcccaaccac gtttacaaag gttcccttac     208
```

-continued

```
gggccgggcg cgcgctgcgc acagtgctcg tatcgctgaa ctcactacgg caaaccgcga    268
aagcggcaac aaatgaaacc tcaaaaaagc ataacattgc ttaagggatc aca atg       324
                                                           Met
                                                           1 cag aac agc gcg atg aag ccc tgg ctg gac tcc tcc tgg ctg gcc ggc      372
Gln Asn Ser Ala Met Lys Pro Trp Leu Asp Ser Ser Trp Leu Ala Gly
              5                  10                  15 gcg aat cag tct tac ata gag caa ctc tat gag gat ttc ctg acc gat      420
Ala Asn Gln Ser Tyr Ile Glu Gln Leu Tyr Glu Asp Phe Leu Thr Asp
         20                  25                  30 cct gac tct gtg gat gca gtg tgg cgc tcg atg ttc caa cag tta cca      468
Pro Asp Ser Val Asp Ala Val Trp Arg Ser Met Phe Gln Gln Leu Pro
     35                  40                  45 ggc acg gga gtg aaa cct gag cag ttc cac tcc gca act cgc gaa tat      516
Gly Thr Gly Val Lys Pro Glu Gln Phe His Ser Ala Thr Arg Glu Tyr
 50                  55                  60                  65 ttc cgt cgc ctg gcg aaa gac gca tct cgt tac acc tcc tca gtt acc      564
Phe Arg Arg Leu Ala Lys Asp Ala Ser Arg Tyr Thr Ser Ser Val Thr
                 70                  75                  80 gat ccg gca acc aac tcc aaa caa gtg aaa gtg ctg cag ctg att aac      612
Asp Pro Ala Thr Asn Ser Lys Gln Val Lys Val Leu Gln Leu Ile Asn
             85                  90                  95 gcg ttt cgt ttc cgc gga cat cag gaa gca aat ctc gat ccg ctt ggc      660
Ala Phe Arg Phe Arg Gly His Gln Glu Ala Asn Leu Asp Pro Leu Gly
         100                 105                 110 ctg tgg aaa cag gac cgc gtt gcc gat ctc gat cct gcc ttt cac gat      708
Leu Trp Lys Gln Asp Arg Val Ala Asp Leu Asp Pro Ala Phe His Asp
 115                 120                 125 ctg acc gac gcc gat ttt cag gaa agc ttt aac gta ggt tct ttt gcc      756
Leu Thr Asp Ala Asp Phe Gln Glu Ser Phe Asn Val Gly Ser Phe Ala
 130                 135                 140                 145 att ggc aaa gaa acc atg aag ctg gcc gat ctg ttc gac gcg ctg aag      804
Ile Gly Lys Glu Thr Met Lys Leu Ala Asp Leu Phe Asp Ala Leu Lys
                 150                 155                 160 cag acc tac tgt ggc tcg att ggt gca gag tat atg cac atc aat aac      852
Gln Thr Tyr Cys Gly Ser Ile Gly Ala Glu Tyr Met His Ile Asn Asn
             165                 170                 175 acc gaa gag aaa cgc tgg atc cag cag cgt atc gaa tcc ggt gcg agc      900
Thr Glu Glu Lys Arg Trp Ile Gln Gln Arg Ile Glu Ser Gly Ala Ser
         180                 185                 190 cag acg tca ttc agt ggc gaa gag aaa aaa ggt ttc ctg aaa gag ctg      948
Gln Thr Ser Phe Ser Gly Glu Glu Lys Lys Gly Phe Leu Lys Glu Leu
 195                 200                 205 acc gcg gca gaa ggg ctg gaa aaa tat ctg ggc gcg aaa ttc ccg ggt      996
Thr Ala Ala Glu Gly Leu Glu Lys Tyr Leu Gly Ala Lys Phe Pro Gly
 210                 215                 220                 225 gca aaa cgt ttc tcg ctg gaa ggc ggt gat gcg ctg gtg ccg atg ctg     1044
Ala Lys Arg Phe Ser Leu Glu Gly Gly Asp Ala Leu Val Pro Met Leu
                 230                 235                 240 cgc gag atg att cgt cat gcg ggc aaa agc ggc aca cgt gaa gtg gta     1092
Arg Glu Met Ile Arg His Ala Gly Lys Ser Gly Thr Arg Glu Val Val
             245                 250                 255 ctg ggg atg gcg cac cgt ggc cgt ctt aac gta ctg att aac gta ctg     1140
Leu Gly Met Ala His Arg Gly Arg Leu Asn Val Leu Ile Asn Val Leu
         260                 265                 270 ggt aaa aag cca cag gat ctg ttc gac gaa ttc tcc ggt aaa cac aaa     1188
Gly Lys Lys Pro Gln Asp Leu Phe Asp Glu Phe Ser Gly Lys His Lys
 275                 280                 285
```

```
gag cat ctg ggc acc ggt gat gtg aag tat cac atg ggc ttc tct tcg    1236
Glu His Leu Gly Thr Gly Asp Val Lys Tyr His Met Gly Phe Ser Ser
290                 295                 300                 305 gat att gaa acc gaa ggt ggt ctg gtg cat ctg gcg ctg gcg ttt aac    1284
Asp Ile Glu Thr Glu Gly Gly Leu Val His Leu Ala Leu Ala Phe Asn
                310                 315                 320 ccg tct cac ctg gaa att gtc agc ccg gtg gtc atg gga tcg gta cgt    1332
Pro Ser His Leu Glu Ile Val Ser Pro Val Val Met Gly Ser Val Arg
            325                 330                 335 gca cgt ctc gat cgt ctg gcc gaa ccg gtc agc aat aaa gtg ttg cct    1380
Ala Arg Leu Asp Arg Leu Ala Glu Pro Val Ser Asn Lys Val Leu Pro
        340                 345                 350 atc acc att cac ggt gat gcg gcg gtg att ggt cag ggc gtg gtt cag    1428
Ile Thr Ile His Gly Asp Ala Ala Val Ile Gly Gln Gly Val Val Gln
    355                 360                 365 gaa acc ctg aac atg tct cag gcg cgc ggc tac gaa gtg ggc ggc acg    1476
Glu Thr Leu Asn Met Ser Gln Ala Arg Gly Tyr Glu Val Gly Gly Thr
370                 375                 380                 385 gta cgt atc gtc att aac aac cag gtt ggt ttt acc acc tcc aac ccg    1524
Val Arg Ile Val Ile Asn Asn Gln Val Gly Phe Thr Thr Ser Asn Pro
                390                 395                 400 aaa gat gcg cgt tca acc ccg tac tgt act gac atc ggc aag atg gtg    1572
Lys Asp Ala Arg Ser Thr Pro Tyr Cys Thr Asp Ile Gly Lys Met Val
            405                 410                 415 ctg gca ccg att ttc cac gtc aat gct gac gat ccg gaa gcg gtg gcc    1620
Leu Ala Pro Ile Phe His Val Asn Ala Asp Asp Pro Glu Ala Val Ala
        420                 425                 430 ttt gtt acc cgc ctg gcg ctg gac tat cgc aac acc ttc aaa cgc gat    1668
Phe Val Thr Arg Leu Ala Leu Asp Tyr Arg Asn Thr Phe Lys Arg Asp
    435                 440                 445 gtg ttt atc gat ctg gtg tgc tat cgc cgt cat ggt cac aac gag gcg    1716
Val Phe Ile Asp Leu Val Cys Tyr Arg Arg His Gly His Asn Glu Ala
450                 455                 460                 465 gat gag cca agt gct acc cag ccg ttg atg tac cag aaa atc aaa aag    1764
Asp Glu Pro Ser Ala Thr Gln Pro Leu Met Tyr Gln Lys Ile Lys Lys
                470                 475                 480 cat ccg acg ccg cgt aaa att tac gcc gat cgt ctg gaa ggc gaa ggt    1812
His Pro Thr Pro Arg Lys Ile Tyr Ala Asp Arg Leu Glu Gly Glu Gly
            485                 490                 495 gtc gcg tcg cag gaa gat gcc acc gag atg gtg aac ctg tac cgc gat    1860
Val Ala Ser Gln Glu Asp Ala Thr Glu Met Val Asn Leu Tyr Arg Asp
        500                 505                 510 gcg ctc gat gcg ggc gaa tgc gtg gtg ccg gaa tgg cgt ccg atg agc    1908
Ala Leu Asp Ala Gly Glu Cys Val Val Pro Glu Trp Arg Pro Met Ser
    515                 520                 525 ctg cac tcc ttc acg tgg tcg cct tat ctg aac cac gaa tgg gat gag    1956
Leu His Ser Phe Thr Trp Ser Pro Tyr Leu Asn His Glu Trp Asp Glu
530                 535                 540                 545 cct tat ccg gca cag gtt gac atg aaa cgc ctg aag gaa ctg gca ttg    2004
Pro Tyr Pro Ala Gln Val Asp Met Lys Arg Leu Lys Glu Leu Ala Leu
                550                 555                 560 cgt atc agc cag gtc cct gag cag att gaa gtg cag tcg cgc gtg gcc    2052
Arg Ile Ser Gln Val Pro Glu Gln Ile Glu Val Gln Ser Arg Val Ala
            565                 570                 575 aag atc tat aac gat cgc aag ctg atg gcc gaa ggc gag aaa gcg ttc    2100
Lys Ile Tyr Asn Asp Arg Lys Leu Met Ala Glu Gly Glu Lys Ala Phe
        580                 585                 590 gac tgg ggc ggt gcc gag aat ctg gcg tac gcc acg ctg gtg gat gaa    2148
Asp Trp Gly Gly Ala Glu Asn Leu Ala Tyr Ala Thr Leu Val Asp Glu
    595                 600                 605
```

```
ggt att ccg gtt cgc ctc tcg ggt gaa gac tcc ggt cgt gga acc ttc      2196
Gly Ile Pro Val Arg Leu Ser Gly Glu Asp Ser Gly Arg Gly Thr Phe
610             615                 620                 625 ttc cat cgc cac gcg gtc gtg cac aac cag gct aac ggt tca acc tat      2244
Phe His Arg His Ala Val Val His Asn Gln Ala Asn Gly Ser Thr Tyr
                630                 635                 640 acg ccg ctg cac cat att cat aac agc cag ggc gag ttc aaa gtc tgg      2292
Thr Pro Leu His His Ile His Asn Ser Gln Gly Glu Phe Lys Val Trp
            645                 650                 655 gat tcg gtg ctg tct gaa gaa gcg gtg ctg gcg ttt gaa tac ggt tac      2340
Asp Ser Val Leu Ser Glu Glu Ala Val Leu Ala Phe Glu Tyr Gly Tyr
        660                 665                 670 gcc acg gct gag ccg cgc gtg ctg acc atc tgg gaa gcg cag ttt ggt      2388
Ala Thr Ala Glu Pro Arg Val Leu Thr Ile Trp Glu Ala Gln Phe Gly
675                 680                 685 gac ttt gcc aac ggt gct cag gtg gtg att gac cag ttc atc agc tct      2436
Asp Phe Ala Asn Gly Ala Gln Val Val Ile Asp Gln Phe Ile Ser Ser
690                 695                 700                 705 ggc gaa cag aag tgg ggc cgt atg tgt ggc ctg gtg atg ttg ctg ccg      2484
Gly Glu Gln Lys Trp Gly Arg Met Cys Gly Leu Val Met Leu Leu Pro
                710                 715                 720 cat ggc tac gaa ggt cag gga ccg gaa cac tcc tct gcc cgt ctg gaa      2532
His Gly Tyr Glu Gly Gln Gly Pro Glu His Ser Ser Ala Arg Leu Glu
            725                 730                 735 cgc tat ctg caa ctt tgc gcc gag cag aac atg cag gtt tgc gtc ccg      2580
Arg Tyr Leu Gln Leu Cys Ala Glu Gln Asn Met Gln Val Cys Val Pro
        740                 745                 750 tcg acg ccg gct cag gtg tat cac atg ctg cgc cgt cag gcg ctg cgc      2628
Ser Thr Pro Ala Gln Val Tyr His Met Leu Arg Arg Gln Ala Leu Arg
755                 760                 765 ggg atg cgc cgt ccg ctg gtg gtg atg tcg ccg aag tcg ctg tta cgc      2676
Gly Met Arg Arg Pro Leu Val Val Met Ser Pro Lys Ser Leu Leu Arg
770                 775                 780                 785 cat cca ctg gcg atc tcg tcg ctg gat gaa ctg gca aac ggc agt ttc      2724
His Pro Leu Ala Ile Ser Ser Leu Asp Glu Leu Ala Asn Gly Ser Phe
                790                 795                 800 cag ccg gcc att ggt gag atc gac gat ctg gat ccg cag ggc gtg aaa      2772
Gln Pro Ala Ile Gly Glu Ile Asp Asp Leu Asp Pro Gln Gly Val Lys
            805                 810                 815 cgc gtc gtg ctg tgc tcc ggt aag gtt tac tac gat ctg ctg gaa cag      2820
Arg Val Val Leu Cys Ser Gly Lys Val Tyr Tyr Asp Leu Leu Glu Gln
        820                 825                 830 cgt cgt aaa gac gag aaa acc gat gtt gcc atc gtg cgc atc gaa cag      2868
Arg Arg Lys Asp Glu Lys Thr Asp Val Ala Ile Val Arg Ile Glu Gln
835                 840                 845 ctt tac ccg ttc ccg cat cag gcg gta cag gaa gca ttg aaa gcc tat      2916
Leu Tyr Pro Phe Pro His Gln Ala Val Gln Glu Ala Leu Lys Ala Tyr
850                 855                 860                 865 tct cac gta cag gac ttt gtc tgg tgc cag gaa gag cct ctg aac cag      2964
Ser His Val Gln Asp Phe Val Trp Cys Gln Glu Glu Pro Leu Asn Gln
                870                 875                 880 ggc gcc tgg tac tgt agc cag cat cat ttc cgt gat gtc gtg ccg ttt      3012
Gly Ala Trp Tyr Cys Ser Gln His His Phe Arg Asp Val Val Pro Phe
            885                 890                 895 ggt gcc acc ctg cgt tat gca ggt cgc ccg gca tcg gct tct ccg gcc      3060
Gly Ala Thr Leu Arg Tyr Ala Gly Arg Pro Ala Ser Ala Ser Pro Ala
        900                 905                 910 gtg ggt tat atg tcc gta cac caa caa cag cag caa gac ctg gtt aat      3108
Val Gly Tyr Met Ser Val His Gln Gln Gln Gln Gln Asp Leu Val Asn
915                 920                 925
```

```
gac gca ctg aac gtc aat taattaaaag gaaagata atg agt agc gta gat    3159
Asp Ala Leu Asn Val Asn                    Met Ser Ser Val Asp
930             935                         1               5 att ctc gtt ccc gac ctg cct gaa tcg gtt gca gat gcc aca gta gca    3207
Ile Leu Val Pro Asp Leu Pro Glu Ser Val Ala Asp Ala Thr Val Ala
                10              15              20 acc tgg cac aag aaa cca ggc gat gca gtc agc cgc gat gaa gtc atc    3255
Thr Trp His Lys Lys Pro Gly Asp Ala Val Ser Arg Asp Glu Val Ile
            25              30              35 gtc gaa att gaa act gac aaa gtc gtg ctg gaa gtg ccg gca tct gcc    3303
Val Glu Ile Glu Thr Asp Lys Val Val Leu Glu Val Pro Ala Ser Ala
        40              45              50 gat ggc gtg ctg gaa gcc gtg ctg gaa gac gaa ggg gca acc gtt acg    3351
Asp Gly Val Leu Glu Ala Val Leu Glu Asp Glu Gly Ala Thr Val Thr
    55              60              65 tcc cgc cag atc ctg ggt cgc ctg aaa gaa ggc aac agt gcg ggt aaa    3399
Ser Arg Gln Ile Leu Gly Arg Leu Lys Glu Gly Asn Ser Ala Gly Lys
70              75              80              85 gaa agc agt gcc aaa gcg gaa agc aat gac acc acg cca gcc cag cgt    3447
Glu Ser Ser Ala Lys Ala Glu Ser Asn Asp Thr Thr Pro Ala Gln Arg
                90              95              100 cag aca gcg tcg ctt gaa gaa gag agc agc gat gcc ctc agc ccg gcg    3495
Gln Thr Ala Ser Leu Glu Glu Glu Ser Ser Asp Ala Leu Ser Pro Ala
            105             110             115 atc cgt cgc ctg att gcg gag cat aat ctt gac gct gcg cag atc aaa    3543
Ile Arg Arg Leu Ile Ala Glu His Asn Leu Asp Ala Ala Gln Ile Lys
        120             125             130 ggc acc ggc gta ggc gga cgt tta acg cgt gaa gac gtt gaa aaa cat    3591
Gly Thr Gly Val Gly Gly Arg Leu Thr Arg Glu Asp Val Glu Lys His
    135             140             145 ctg gcg aac aaa ccg cag gct gag aaa gcc gcc gcg cca gcg gcg ggt    3639
Leu Ala Asn Lys Pro Gln Ala Glu Lys Ala Ala Ala Pro Ala Ala Gly
150             155             160             165 gca gca acg gct cag cag cct gtt gcc aac cgc agc gaa aaa cgt gtt    3687
Ala Ala Thr Ala Gln Gln Pro Val Ala Asn Arg Ser Glu Lys Arg Val
                170             175             180 ccg atg acg cgt tta cgt aag cgc gtc gcg gag cgt ctg ctg gaa gcc    3735
Pro Met Thr Arg Leu Arg Lys Arg Val Ala Glu Arg Leu Leu Glu Ala
            185             190             195 aag aac agc acc gcc atg ttg acg acc ttc aac gaa atc aac atg aag    3783
Lys Asn Ser Thr Ala Met Leu Thr Thr Phe Asn Glu Ile Asn Met Lys
        200             205             210 ccg att atg gat ctg cgt aag cag tac ggc gat gcg ttc gag aag cgt    3831
Pro Ile Met Asp Leu Arg Lys Gln Tyr Gly Asp Ala Phe Glu Lys Arg
215             220             225 cac ggt gtg cgt ctg ggc ttt atg tct ttc tac atc aag gcc gtg gtc    3879
His Gly Val Arg Leu Gly Phe Met Ser Phe Tyr Ile Lys Ala Val Val
230             235             240             245 gaa gcg ctg aag cgt tat cca gaa gtc aac gcc tct atc gat ggc gaa    3927
Glu Ala Leu Lys Arg Tyr Pro Glu Val Asn Ala Ser Ile Asp Gly Glu
                250             255             260 gac gtg gtg tac cac aac tat ttc gat gtg agt att gcc gtc tct acg    3975
Asp Val Val Tyr His Asn Tyr Phe Asp Val Ser Ile Ala Val Ser Thr
            265             270             275 cca cgc gga ctg gtg acg cct gtc ctg cgt gac gtt gat gcg ctg agc    4023
Pro Arg Gly Leu Val Thr Pro Val Leu Arg Asp Val Asp Ala Leu Ser
        280             285             290 atg gct gac atc gag aag aaa att aaa gaa ctg gca gtg aaa ggc cgt    4071
Met Ala Asp Ile Glu Lys Lys Ile Lys Glu Leu Ala Val Lys Gly Arg
295             300             305
```

-continued

```
gac ggc aag ctg acg gtt gac gat ctg acg ggc ggt aac ttt acc atc     4119
Asp Gly Lys Leu Thr Val Asp Asp Leu Thr Gly Gly Asn Phe Thr Ile
310                 315                 320                 325 acc aac ggt ggt gtg ttc ggt tcg ctg atg tct acg cca atc atc aac     4167
Thr Asn Gly Gly Val Phe Gly Ser Leu Met Ser Thr Pro Ile Ile Asn
                330                 335                 340 ccg cca cag agc gcg att ctg ggc atg cac gcc att aaa gat cgt cct     4215
Pro Pro Gln Ser Ala Ile Leu Gly Met His Ala Ile Lys Asp Arg Pro
            345                 350                 355 atg gcg gtc aat ggt cag gtt gtg atc ctg cca atg atg tac ctg gct     4263
Met Ala Val Asn Gly Gln Val Val Ile Leu Pro Met Met Tyr Leu Ala
        360                 365                 370 ctc tcc tac gat cac cgt tta atc gat ggt cgt gaa tct gtc ggc tat     4311
Leu Ser Tyr Asp His Arg Leu Ile Asp Gly Arg Glu Ser Val Gly Tyr
    375                 380                 385 ctg gtc gcg gtg aaa gag atg ctg gaa gat ccg gcg cgt ctg ctg ctg     4359
Leu Val Ala Val Lys Glu Met Leu Glu Asp Pro Ala Arg Leu Leu Leu
390                 395                 400                 405 gat gtc tgattcatca ctgggcacgc gttgcgtgcc caatctcaat actcttttca      4415
Asp Val gatctgaatg gatagaacat c atg aac tta cac gaa tac cag gct aaa cag     4466
                        Met Asn Leu His Glu Tyr Gln Ala Lys Gln
                          1               5                  10 ctg ttt gca cgg tat ggc atg cca gca ccg acc ggc tac gcc tgt act     4514
Leu Phe Ala Arg Tyr Gly Met Pro Ala Pro Thr Gly Tyr Ala Cys Thr
                15                  20                  25 aca cca cgt gaa gca gaa gaa gcg gca tcg aaa atc ggt gca             4556
Thr Pro Arg Glu Ala Glu Glu Ala Ala Ser Lys Ile Gly Ala
            30                  35                  40

<210> SEQ ID NO 2
<211> LENGTH: 39
<212> TYPE: PRT
<213> ORGANISM: Pantoea ananatis

<400> SEQUENCE: 2

Ala Phe Ser Val Phe Arg Cys His Ser Ile Met Asn Cys Val Ser Val
  1               5                  10                  15

Cys Pro Lys Gly Leu Asn Pro Thr Arg Ala Ile Gly His Ile Lys Ser
            20                  25                  30

Met Leu Leu Gln Arg Ser Ala
        35

<210> SEQ ID NO 3
<211> LENGTH: 935
<212> TYPE: PRT
<213> ORGANISM: Pantoea ananatis

<400> SEQUENCE: 3

Met Gln Asn Ser Ala Met Lys Pro Trp Leu Asp Ser Ser Trp Leu Ala
  1               5                  10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
 65                  70                  75                  80
```

-continued

```
Thr Asp Pro Ala Thr Asn Ser Lys Gln Val Lys Val Leu Gln Leu Ile
                 85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175

Asn Thr Glu Glu Lys Arg Trp Ile Gln Gln Arg Ile Glu Ser Gly Ala
            180                 185                 190

Ser Gln Thr Ser Phe Ser Gly Glu Lys Lys Gly Phe Leu Lys Glu
        195                 200                 205

Leu Thr Ala Ala Glu Gly Leu Glu Lys Tyr Leu Gly Ala Lys Phe Pro
    210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
        275                 280                 285

Lys Glu His Leu Gly Thr Gly Asp Val Lys Tyr His Met Gly Phe Ser
    290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Val Ile Gly Gln Gly Val Val
        355                 360                 365

Gln Glu Thr Leu Asn Met Ser Gln Ala Arg Gly Tyr Glu Val Gly Gly
    370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
        435                 440                 445

Asp Val Phe Ile Asp Leu Val Cys Tyr Arg Arg His Gly His Asn Glu
    450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
                485                 490                 495
```

-continued

```
Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
        515                 520                 525

Ser Leu His Ser Phe Thr Trp Ser Pro Tyr Leu Asn His Glu Trp Asp
    530                 535                 540

Glu Pro Tyr Pro Ala Gln Val Asp Met Lys Arg Leu Lys Glu Leu Ala
545                 550                 555                 560

Leu Arg Ile Ser Gln Val Pro Glu Gln Ile Glu Val Gln Ser Arg Val
                565                 570                 575

Ala Lys Ile Tyr Asn Asp Arg Lys Leu Met Ala Glu Gly Glu Lys Ala
            580                 585                 590

Phe Asp Trp Gly Gly Ala Glu Asn Leu Ala Tyr Ala Thr Leu Val Asp
        595                 600                 605

Glu Gly Ile Pro Val Arg Leu Ser Gly Glu Asp Ser Gly Arg Gly Thr
    610                 615                 620

Phe Phe His Arg His Ala Val Val His Asn Gln Ala Asn Gly Ser Thr
625                 630                 635                 640

Tyr Thr Pro Leu His His Ile His Asn Ser Gln Gly Glu Phe Lys Val
                645                 650                 655

Trp Asp Ser Val Leu Ser Glu Glu Ala Val Leu Ala Phe Glu Tyr Gly
            660                 665                 670

Tyr Ala Thr Ala Glu Pro Arg Val Leu Thr Ile Trp Glu Ala Gln Phe
        675                 680                 685

Gly Asp Phe Ala Asn Gly Ala Gln Val Val Ile Asp Gln Phe Ile Ser
    690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
                725                 730                 735

Glu Arg Tyr Leu Gln Leu Cys Ala Glu Gln Asn Met Gln Val Cys Val
            740                 745                 750

Pro Ser Thr Pro Ala Gln Val Tyr His Met Leu Arg Arg Gln Ala Leu
        755                 760                 765

Arg Gly Met Arg Arg Pro Leu Val Val Met Ser Pro Lys Ser Leu Leu
    770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
                805                 810                 815

Lys Arg Val Val Leu Cys Ser Gly Lys Val Tyr Tyr Asp Leu Leu Glu
            820                 825                 830

Gln Arg Arg Lys Asp Glu Lys Thr Asp Val Ala Ile Val Arg Ile Glu
        835                 840                 845

Gln Leu Tyr Pro Phe Pro His Gln Ala Val Gln Glu Ala Leu Lys Ala
    850                 855                 860

Tyr Ser His Val Gln Asp Phe Val Trp Cys Gln Glu Glu Pro Leu Asn
865                 870                 875                 880

Gln Gly Ala Trp Tyr Cys Ser Gln His His Phe Arg Asp Val Val Pro
                885                 890                 895

Phe Gly Ala Thr Leu Arg Tyr Ala Gly Arg Pro Ala Ser Ala Ser Pro
            900                 905                 910
```

-continued

Ala Val Gly Tyr Met Ser Val His Gln Gln Gln Gln Asp Leu Val
        915                 920                 925

Asn Asp Ala Leu Asn Val Asn
    930                 935

<210> SEQ ID NO 4
<211> LENGTH: 407
<212> TYPE: PRT
<213> ORGANISM: Pantoea ananatis

<400> SEQUENCE: 4

Met Ser Ser Val Asp Ile Leu Val Pro Asp Leu Pro Glu Ser Val Ala
  1               5                  10                  15

Asp Ala Thr Val Ala Thr Trp His Lys Lys Pro Gly Asp Ala Val Ser
             20                  25                  30

Arg Asp Glu Val Ile Val Glu Ile Glu Thr Asp Lys Val Val Leu Glu
         35                  40                  45

Val Pro Ala Ser Ala Asp Gly Val Leu Glu Ala Val Leu Glu Asp Glu
     50                  55                  60

Gly Ala Thr Val Thr Ser Arg Gln Ile Leu Gly Arg Leu Lys Glu Gly
 65                  70                  75                  80

Asn Ser Ala Gly Lys Glu Ser Ser Ala Lys Ala Glu Ser Asn Asp Thr
                 85                  90                  95

Thr Pro Ala Gln Arg Gln Thr Ala Ser Leu Glu Glu Glu Ser Ser Asp
            100                 105                 110

Ala Leu Ser Pro Ala Ile Arg Arg Leu Ile Ala Glu His Asn Leu Asp
        115                 120                 125

Ala Ala Gln Ile Lys Gly Thr Gly Val Gly Gly Arg Leu Thr Arg Glu
    130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
    210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Lys Ile Lys Glu Leu
    290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
            340                 345                 350

-continued

```
Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
    370                 375                 380

Glu Ser Val Gly Tyr Leu Val Ala Val Lys Glu Met Leu Glu Asp Pro
385                 390                 395                 400

Ala Arg Leu Leu Leu Asp Val
                405

<210> SEQ ID NO 5
<211> LENGTH: 40
<212> TYPE: PRT
<213> ORGANISM: Pantoea ananatis

<400> SEQUENCE: 5

Met Asn Leu His Glu Tyr Gln Ala Lys Gln Leu Phe Ala Arg Tyr Gly
  1               5                  10                  15

Met Pro Ala Pro Thr Gly Tyr Ala Cys Thr Thr Pro Arg Glu Ala Glu
             20                  25                  30

Glu Ala Ala Ser Lys Ile Gly Ala
         35                  40

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
gtcgacaata gccygaatct gttctggtcg                                       30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
aagcttatcg acgctcccct ccccaccgtt                                       30

<210> SEQ ID NO 8
<211> LENGTH: 16214
<212> TYPE: DNA
<213> ORGANISM: Artificial Sequence
<220> FEATURE:
<223> OTHER INFORMATION: plasmid RSFCPG

<400> SEQUENCE: 8
gaattccgcc agaaccttca tcagcagcat aaacaggtgc agtgaacagc agagatacgg     60
ccagtgcggc caatgttttt tgtcctttaa acataacaga gtcctttaag gatatagaat    120
aggggtatag ctacgccaga atatcgtatt tgattattgc tagttttttag ttttgcttaa    180 aaaatattgt tagttttatt aaattggaaa actaaattat tggtatcatg aattgttgta    240
tgatgataaa tatagggggg atatgataga cgtcattttc atagggttat aaaatgcgac    300
taccatgaag ttttttaattc aaagtattgg gttgctgata atttgagctg ttctattctt    360
tttaaatatc tataggtc tgttaatgga tttattttt acaagttttt tgtgtttagg    420
catataaaaa tcaagcccgc catatgaacg gcgggttaaa atatttacaa cttagcaatc    480
```

-continued

| | |
|---|---|
| gaaccattaa cgcttgatat cgcttttaaa gtcgcgtttt tcatatcctg tatacagctg | 540 |
| acgcggacgg gcaatcttca taccgtcact gtgcatttcg ctccagtggg cgatccagcc | 600 |
| aacggtacgt gccattgcga aaatgacggt gaacatggaa gacggaatac ccatcgcttt | 660 |
| caggatgata ccagagtaga aatcgacgtt cgggtacagt ttcttctcga taaagtacgg | 720 |
| gtcgttcagc gcgatgtttt ccagctccat agccacttcc agcaggtcat ccttcgtgcc | 780 |
| cagctctttc agcacttcat ggcaggtttc acgcattacg gtggcgcgcg ggtcgtaatt | 840 |
| tttgtacacg cggtgaccga agcccatcag gcggaaagaa tcattttgt ctttcgcacg | 900 |
| acgaaaaaat tccggaatgt gtttaacgga gctgatttct tccagcattt tcagcgccgc | 960 |
| ttcgttagca ccgccgtgcg caggtcccca cagtgaagca atacctgctg cgatacaggc | 1020 |
| aaacgggttc gcacccgaag agccagcggt acgcacggtg gaggtagagg cgttctgttc | 1080 |
| atggtcagcg tgcaggatca gaatacggtc catagcacgt tccagaatcg gattaacttc | 1140 |
| atacggttcg cacggcgtgg agaacatcat attcaggaag ttaccggcgt aggagagatc | 1200 |
| gttgcgcggg taaacaaatg gctgaccaat ggaatacttg taacacatcg cggccatggt | 1260 |
| cggcattttc gacagcaggc ggaacgcggc aatttcacgg tgacgaggat tgttaacatc | 1320 |
| cagcgagtcg tgatagaacg ccgccagcgc gccggtaata ccacacatga ctgccattgg | 1380 |
| atgcgagtcg cgacggaaag catggaacag acgggtaatc tgctcgtgga tcatggtatg | 1440 |
| acgggtcacc gtagttttaa attcgtcata ctgttcctga gtcggttttt caccattcag | 1500 |
| caggatgtaa caaacttcca ggtagttaga atcggtcgcc agctgatcga tcgggaaacc | 1560 |
| gcggtgcagc aaaataccct catcaccatc aataaaagta attttagatt cgcaggatgc | 1620 |
| ggttgaagtg aagcctgggt caaaggtgaa cacacctttt gaaccgagag tacggatatc | 1680 |
| aataacatct tgacccagcg tgcctttcag cacatccagt tcaacagctg tatccccgtt | 1740 |
| gagggtgagt tttgcttttg tatcagccat ttaaggtctc cttagcgcct tattgcgtaa | 1800 |
| gactgccgga acttaaattt gccttcgcac atcaacctgg cttaaccgt tttttatttg | 1860 |
| gctcgccgct ctgtgaaaga ggggaaaacc tgggtacaga gctctgggcg cttgcaggta | 1920 |
| aaggatccat tgatgacgaa taaatggcga atcaagtact tagcaatccg aattattaaa | 1980 |
| cttgtctacc actaataact gtcccgaatg aattggtcaa tactccacac tgttacataa | 2040 |
| gttaatctta ggtgaaatac cgacttcata acttttacgc attatatgct tttcctggta | 2100 |
| atgtttgtaa caactttgtt gaatgattgt caaattagat gattaaaaat taaataaatg | 2160 |
| ttgttatcgt gacctggatc actgttcagg ataaaacccg acaaactata tgtaggttaa | 2220 |
| ttgtaatgat tttgtgaaca gcctatactg ccgccagtct ccggaacacc ctgcaatccc | 2280 |
| gagccaccca gcgttgtaac gtgtcgtttt cgcatctgga agcagtgttt tgcatgacgc | 2340 |
| gcagttatag aaaggacgct gtctgacccg caagcagacc ggaggaagga atcccgacg | 2400 |
| tcggggatcc tctagagctt tagcgtctga ggttatcgca atttggttat gagattactc | 2460 |
| tcgttattaa tttgctttcc tgggtcattt ttttcttgct taccgtcaca ttcttgatgg | 2520 |
| tatagtcgaa aactgcaaaa gcacatgaca taaacaacat aagcacaatc gtattaatat | 2580 |
| ataagggttt tatatctatg gatcagacat attctctgga gtcattcctc aaccatgtcc | 2640 |
| aaaagcgcga cccgaatcaa accgagttcg cgcaagccgt tcgtgaagta atgaccacac | 2700 |
| tctggccttt tcttgaacaa aatccaaaat atcgccagat gtcattactg gagcgtctgg | 2760 |
| ttgaaccgga gcgcgtgatc cagtttcgcg tggtatgggt tgatgatcgc aaccagatac | 2820 |

```
aggtcaaccg tgcatggcgt gtgcagttca gctctgccat cggcccgtac aaaggcggta    2880
tgcgcttcca tccgtcagtt aacctttcca ttctcaaatt cctcggcttt gaacaaacct    2940
tcaaaaatgc cctgactact ctgccgatgg gcggtggtaa aggcggcagc gatttcgatc    3000
cgaaaggaaa aagcgaaggt gaagtgatgc gttttttgcca ggcgctgatg actgaactgt   3060
atcgccacct gggcgcggat accgacgttc cggcaggtga tatcgggatt ggtggtcgtg    3120
aagtcggctt tatggcgggg atgatgaaaa agctctccaa caataccgcc tgcgtcttca    3180
ccggtaaggg cctttcattt ggcggcagtc ttattcgccc ggaagctacc ggctacggtc    3240
tggtttattt cacagaagca atgctaaaac gccacgtat gggttttgaa gggatgcgcg     3300
tttccgtttc tggctccggc aacgtcgccc agtacgctat cgaaaagcg atggaatttg     3360
gtgctcgtgt gatcactgcg tcagactcca gcggcactgt agttgatgaa gcggattca    3420
cgaaagagaa actggcacgt cttatcgaaa tcaaagccag ccgcgatggt cgagtggcag    3480
attacgccaa agaatttggt ctggtctatc tcgaaggcca acagccgtgg tctctaccgg    3540
ttgatatcgc cctgccttgc gccacccaga tgaactgga tgttgacgcc gcgcatcagc    3600
ttatcgctaa tggcgttaaa gccgtcgccg aaggggcaaa tatgccgacc accatcgaag   3660
cgactgaact gttccagcag gcaggcgtac tatttgcacc gggtaaagcg gctaatgctg    3720
gtggcgtcgc tacatcgggc ctggaaatgc acaaaacgc tgcgcgcctg ggctggaaag    3780
ccgagaaagt tgacgcacgt ttgcatcaca tcatgctgga tatccaccat gcctgtgttg    3840
agcatggtgg tgaaggtgag caaaccaact acgtgcaggg cgcgaacatt gccggtttg   3900
tgaaggttgc cgatgcgatg ctggcgcagg gtgtgattta agttgtaaat gcctgatggc    3960
gctacgctta tcaggcctac aaatgggcac aattcattgc agttacgctc taatgtaggc    4020
cgggcaagcg cagcgccccc ggcaaaattt caggcgttta tgagtattta acggatgatg   4080
ctccccacgg aacatttctt atgggccaac ggcatttctt actgtagtgc tcccaaaact    4140
gcttgtcgta acgataacac gcttcaagtt cagcatccgt taactttctg cggactcacg    4200
cgcgcagcac tatgccagta aagaaatccc atttgactat ttttttgata atcttcttcg    4260
ctttcgaaca actcgtgcgc ctttcgagaa gctagagtcg actcgccaat caccagcact    4320
aaagtgcgcg gttcgttacc cgattcatct ttgaaattag ccagtggcgg caaggcatta    4380
ttttcattca gtaactttgt tagcgagttt agttgctgac gatactgata tagccggtc     4440
aggaattgcc acgtgcggc aggctccata cgcgaggcca ggttatccaa cgttttctca    4500
aacggcttgt ttttgataaa cgtattcatg gcgatcggat gcagaatcaa gccataaagc    4560
agggcaaaag agacaacata cgccacggc tttggaatat agaccgggcg caggcgtgtc     4620
cacagcagaa ctgccaccgc cgtataggcc agcgcgataa gcacaatttt caggctgaaa    4680
tactggctta atactcgct ggcttcgttg gtgttggttt cgaacatcac aaacagaacg     4740
ctctgcgaga actcctgacc gtagatgacg tagtagcaca gcgccgccag agaggccgcc    4800
catagcacca cgccgattac tgcggcaata attttaatcc gcttcggaaa gaggaatacc    4860
gggatcaacc acagcgaact gaataacagc gagtcgcgaa tgccgttagt gccactataa    4920
ccactgatgt aaataatggc ctgtagcaga gtagagaaaa accaaaagta gagcagtgcc    4980
caacccaggc ctttccagct aaaaagaggt ttagcctgga cttctgtgga atgcatagta    5040
agaacctgtc ttgaaaaaat atcgccgaat gtaacgacaa ttccttaagg atatctgaag    5100
gtatattcag aatttgaata aaatgcagac agaaatatat tgaaaacgag ggtgttagaa    5160
cagaagtatt tcagaaaacc ctcgcgcaaa agcacgaggg tttgcagaag aggaagatta    5220
```

```
gccggtatta cgcatacctg ccgcaatccc ggcaatagtg accattaacg cttgttcgac   5280
gcgaggatcc ggttcctggc cttcttttc tgcctggcgg gagcggtgca gcaactcggc    5340
ctgcaatacg ttcagcgggt cggtgtaaat attccgtagc tgaatagact ctgcaatcca   5400
cggcagatcg gccatcagat gggaatcgtt ggcaatcgcc agcaccactt tgatgtcttc   5460
ttcttgcagg ttgcgtaact ctttacctaa cggccacagt gctttgtcta ccaggcgttg   5520
gtcatagtat tccgccagcc acaggtctgc tttggcgaag accatctcca gcatgccgag   5580
acgcgtcgag aagaatggcc aatcgcggca catagcctcc agctcgctct gtttgccgtc   5640
ttcgaccact ttttgcagcg ccgtacctgc acccagccag gcggggagca tcagacggtt   5700
ttgcgtccag gcgaagatcc acggaatggc gcgtagtgac tcgacgccgc cggttgggcg   5760
acgtttcgcc ggacgtgaac ccaacggcag tttgcccagt tcttgttccg gcgtagcgga   5820
gcggaagtaa ggcacaaaat ctttgttttc acgtacgtag ccgcggtaga catcgcagga   5880
gatgactgac agttcatcca taatgcgacg ccagctctct ttcggctccg gcggtggcag   5940
caggttggct tccagaatcg ccccggtata aagcgacagg ctgctgacgg tgatttctgg   6000
cagaccatat ttaaagcgga tcatctcgcc ctgttcggtt acgcgcaggc cgcctttcag   6060
gcttcctggc ggttgtgaca gcagcgccgc atgagcaggt gcgccgccgc gaccaatgga   6120
accgccgcga ccgtggaaca acgtcagctc aatacccgct ttttcgcagg ttttgattaa   6180
tgcatcctgt gcctgatatt gcgcccagga agctgccatc actcccgcat cttttgctga   6240
gtcggaatag ccaatcatca ccatctgttt gccctgaatc aggccacgat accagtcaat   6300
attgagcagc tgggtcatga catcgttggc gttgttcaga tcatcgaggg tttcaaacag   6360
cggagcaacc ggcatcgcaa acccgatacc cgcttctttc agcagcaggt ggacagccaa   6420
tacgtcggac ggcgttttcg ccatcgagat cacgtaggcg gcaatggagc cttgcggtgc   6480
ttcggcaatc acctggcagg tatcgagcac ttcgcgcgtt tcggcgcttg gttgccagtt   6540
gcgcggcaga agcggacgtt tggagttcag ttcgcggatc aggaacgcct gtttgtcggc   6600
ctctgaccag ctttcgtagt cgccgatacc gaggtagcgg gtcagctcgc ccagcgcttc   6660
ggtatgacgc gtgctctcct gacggatatc aatacggacc agcggtacgc cgaaacattt   6720
cacgcggcgc agggtgtcga gcagatcgcc gttggcgata atacccatgc cacacgcctg   6780
aagtgactgg tagcaagcgt agagcggttc ccacagttct tcgtttttgtg tcagcaggcc   6840 ttctggtttt ggcagttctt cgcctttcag gcgcgcttcc agccatgcct gtgtcgccat   6900
caggcgagaa cgcaggtttt tcatcagata gcgatacggt tctgcggcac cttcttcgcc   6960
aaccagcgcc agcagttcag gggtcgcttc aaccatcgac agttcagaaa ccagcacctg   7020
aatatctttc aggaacaaat cggtggcttt ccagcggctg agtagcagga cgtggcgggt   7080
gatatcggca gtgacgttcg ggttgccgtc gcggtcgccg cccatccacg aagtaaaacg   7140
gaccggaaca aattcgacgg gcagtttgta gccgaggttc tcttccagtt gttcgttcag   7200
ttcgcgcagg taatttggta cgccttgcca caggctgttt tccactacgg caaagcccca   7260
tttggcttca tctaccgggc ttggacgcag cttacggatt tcatcggtat gccatgactg   7320
ggcgatcaac tggcgcaggc gacgcatcag ctggttgtgt tcgtagtcag cgatatcttt   7380
gttatcgagc tgtttttaaac aggcgttcac ttccaccatt ttgtggatca gtgtacgacg   7440
ggtaatttcg gttgggtgag ccgtgaggac cagttccagc gacagcgatt ccactgcttt   7500
tttgatggtg tcttcgctca gttccggctg gttttttcagt ttacgcaggg tgcgggcgat   7560
```

```
cacttccggg ttgctggcag cttcgccttt cggcgaaatg ctgtggtatt gctcggcggt    7620
gttggccagg ttcaggaact gactaaacgc acgcgcaacg ggcagcagct cgtcgttcga    7680
caaattttgt aaggtggtga gcaactcctg gcggttagca tcattgccag cgcgtgaaga    7740
tttcgacaac ttacggatag tttctacgcg ttcaagaatg tgttctccca acgcatcctt    7800
gatggtttct cccagcactt tgccgagcat actgacatta ctacgcaatg cggaatattg    7860
ttcgttcata ttaccccaga caccccatct tatcgtttga tagccctgta tccttcacgt    7920
cgcattggcg cgaatatgct cgggctttgc ttttcgtcgt cttttataaa gccacgtaaa    7980
agcggtgacg tcaaatgctg cgaaatcgct tcagcaaacg aataaatagc aggaatttac    8040
gtcattaaat tcacgacgct ttaaataagc gtaacttatg gaaatgttaa aaaatcgccc    8100
caagtaacac caaaggtgta ggtcggataa gatgcgcaag tatcgcatcc gacattattg    8160
cggcactgga gtttggcaac agtgccggat gcggcgcgag cgccttatcc ggcctacagt    8220
tgggcatcgt ttgagtcact gtcggtcgga taagatgcgc aagtatcgca tccgacatta    8280
ttgcggcact ggagtttggc aacagtgccg gatgcggcgc gagcgcctta tccggcctac    8340
ggttgggcat cgtttgagtc actgtaggtc ggataagatg cgcaagcatc gcatccgaca    8400
ttattgcggc actggagttt ggcaacagcg ccggatgcgg cgcgagcgcc ttatccggcc    8460
tacgttttaa tgccagcaaa aatggtgaat tacctgggtt atcagttcgc gggtgggctt    8520
gataaaccgt gtttccagat attcatcagg ttgatgagcc tgattaattg agccaggccc    8580
caacaccagc gtcgggcata acgtttgaat aaacggcgct tcggtacagt agttcaccac    8640
ttcggttttt gctccgagca atttctcaac cacttcaacc agttgatgat tcggtgggca    8700
ttcatagcca gggatcggcg gatgcagctc gtcgacctgc aggagcagaa gagcatacat    8760
ctggaagcaa agccaggaaa gcggcctatg gagctgtgcg gcagcgctca gtaggcaatt    8820
tttcaaaata ttgttaagcc ttttctgagc atggtatttt tcatggtatt accaattagc    8880
aggaaaataa gccattgaat ataaaagata aaaatgtctt gtttacaata gagtgggggg    8940
ggtcagcctg ccgccttggg ccgggtgatg tcgtacttgc ccgccgcgaa ctcggttacc    9000
gtccagccca gcgcgaccag ctccggcaac gcctcgcgca cccgctggcg gcgcttgcgc    9060
atggtcgaac cactggcctc tgacggccag acatagccgc acaaggtatc tatgcaagcc    9120
ttgccggttt tgccggggtc gatccagcca cacagccgct ggtgcagcag gcgggcggtt    9180
tcgctgtcca gcgcccgcac ctcgtccatg ctgatgcgca catgctggcc gccacccatg    9240
acggcctgcg cgatcaaggg gttcagggcc acgtacaggc gcccgtccgc ctcgtcgctg    9300
gcgtactccg acagcagccg aaaccccctgc cgcttgcggc cattctgggc gatgatggat    9360
accttccaaa ggcgctcgat gcagtcctgt atgtgcttga gcgccccacc actatcgacc    9420
tctgccccga tttcctttgc cagcgcccga tagctacctt tgaccacatg gcattcagcg    9480
gtgacggcct cccacttggg ttccaggaac agccggagct gccgtccgcc ttcggtcttg    9540
ggttccgggc caagcactag gccattaggc ccagccatgg ccaccagccc ttgcaggatg    9600
cgcagatcat cagcgcccag cggctccggg ccgctgaact cgatccgctt gccgtcgccg    9660
tagtcatacg tcacgtccag cttgctgcgc ttgcgctcgc cccgcttgag ggcacggaac    9720
aggccggggg ccagacagtg cgccgggtcg tgccggacgt ggctgaggct gtgcttgttc    9780
ttaggcttca ccacggggca ccccttgct cttgcgctgc ctctccagca cggcgggctt    9840
gagcaccccg ccgtcatgcc gcctgaacca ccgatcagcg aacggtgcgc catagttggc    9900
cttgctcaca ccgaagcgga cgaagaaccg gcgctggtcg tcgtccacac cccattcctc    9960
```

```
ggcctcggcg ctggtcatgc tcgacaggta ggactgccag cggatgttat cgaccagtac   10020
cgagctgccc cggctggcct gctgctggtc gcctgcgccc atcatggccg cgcccttgct   10080
ggcatggtgc aggaacacga tagagcaccc ggtatcggcg gcgatggcct ccatgcgacc   10140
gatgacctgg gccatggggc cgctggcgtt ttcttcctcg atgtggaacc ggcgcagcgt   10200
gtccagcacc atcaggcggc ggccctcggc ggcgcgcttg aggccgtcga accactccgg   10260
ggccatgatg ttgggcaggc tgccgatcag cggctggatc agcaggccgt cagccacggc   10320
ttgccgttcc tcgcgctga ggtgcgcccc aagggcgtgc aggcggtgat gaatggcggt   10380
gggcgggtct tcggcgggca ggtagatcac cgggccggtg ggcagttcgc ccacctccag   10440
cagatccggc ccgcctgcaa tctgtgcggc cagttgcagg gccagcatgg atttaccggc   10500
accaccgggc gacaccagcg ccccgaccgt accggccacc atgttgggca aaacgtagtc   10560
cagcggtggc ggcgctgctg cgaacgcctc cagaatattg ataggcttat gggtagccat   10620
tgattgcctc ctttgcaggc agttggtggt taggcgctgg cggggtcact accccgccc    10680 tgcgccgctc tgagttcttc caggcactcg cgcagcgcct cgtattcgtc gtcggtcagc   10740
cagaacttgc gctgacgcat cccttttggcc ttcatgcgct cggcatatcg cgcttggcgt   10800
acagcgtcag ggctggccag caggtcgccg gtctgcttgt cctttttggtc tttcatatca   10860 gtcaccgaga aacttgccgg ggccgaaagg cttgtcttcg cggaacaagg acaaggtgca   10920
gccgtcaagg ttaaggctgg ccatatcagc gactgaaaag cggccagcct cggccttgtt   10980
tgacgtataa ccaaagccac cgggcaacca atagcccttg tcacttttga tcaggtagac   11040
cgaccctgaa gcgcttttttt cgtattccat aaaaccccct tctgtgcgtg agtactcata   11100
gtataacagg cgtgagtacc aacgcaagca ctacatgctg aaatctggcc cgcccctgtc   11160
catgcctcgc tggcggggtg ccggtgcccg tgccagctcg gcccgcgcaa gctggacgct   11220
gggcagaccc atgaccttgc tgacggtgcg ctcgatgtaa tccgcttcgt ggcccgggctt  11280 gcgctctgcc agcgctgggc tggcctcggc catggccttg ccgatttcct cggcactgcg   11340
gccccggctg gccagcttct gcgcggcgat aaagtcgcac ttgctgaggt catcaccgaa   11400
gcgcttgacc agcccggcca tctcgctgcg gtactcgtcc agcgccgtgc gccggtggcg   11460
gctaagctgc cgctcgggca gttcgaggct ggccagcctg cgggccttct cctgctgccg   11520
ctgggcctgc tcgatctgct ggccagcctg ctgcaccagc gccgggccag cggtggcggt   11580
cttgcccttg gattcacgca gcagcaccca cggctgataa ccggcgcggg tggtgtgctt   11640
gtccttgcgg ttggtgaagc ccgccaagcg gccatagtgg cggctgtcgg cgctggccgg   11700
gtcggcgtcg tactcgctgg ccagcgtccg ggcaatctgc ccccgaagtt caccgcctgc   11760
ggcgtcggcc accttgaccc atgcctgata gttcttcggg ctggtttcca ctaccagggc   11820
aggctcccgg ccctcggctt tcatgtcatc caggtcaaac tcgctgaggt cgtccaccag   11880
caccagacca tgccgctcct gctcggcggg cctgatatac acgtcattgc cctgggcatt   11940
catccgcttg agccatggcg tgttctggag cacttcggcg gctgaccatt cccggttcat   12000
catctggccg gtggtggcgt ccctgacgcc gatatcgaag cgctcacagc ccatggcctt   12060
gagctgtcgg cctatggcct gcaaagtcct gtcgttcttc atcgggccac caagcgcagc   12120
cagatcgagc cgtcctcggt tgtcagtggc gtcaggtcga gcaagagcaa cgatgcgatc   12180
agcagcacca ccgtaggcat catggaagcc agcatcacgg ttagccatag cttccagtgc   12240
cacccccgcg acgcgctccg ggcgctctgc gcggcgctgc tcacctcggc ggctaccctcc   12300
```

```
cgcaactctt tggccagctc cacccatgcc gccctgtct ggcgctgggc tttcagccac   12360
tccgccgcct gcgcctcgct ggcctgctgg gtctggctca tgacctgccg ggcttcgtcg   12420
gccagtgtcg ccatgctctg ggccagcggt tcgatctgct ccgctaactc gttgatgcct   12480
ctggatttct tcactctgtc gattgcgttc atggtctatt gcctcccggt attcctgtaa   12540
gtcgatgatc tgggcgttgg cggtgtcgat gttcagggcc acgtctgccc ggtcggtgcg   12600
gatgccccgg ccttccatct ccaccacgtt cggcccagg tgaacaccgg gcaggcgctc    12660
gatgccctgc gcctcaagtg ttctgtggtc aatgcgggcg tcgtggccag cccgctctaa   12720
tgcccggttg gcatggtcgg cccatgcctc gcgggtctgc tcaagccatg ccttgggctt   12780
gagcgcttcg gtcttctgtg ccccgccctt ctccggggtc ttgccgttgt accgcttgaa   12840
ccactgagcg gcgggccgct cgatgccgtc attgatccgc tcggagatca tcaggtggca   12900
gtgcgggttc tcgccgccac cggcatggat ggccagcgta acggcaggc gctcggcacc   12960 ggtcaggtgc tgggcgaact cggacgccag cgccttctgc tggtcgaggg tcagctcgac   13020
cggcagggca aattcgacct ccttgaacag ccgcccattg gcgcgttcat acaggtcggc   13080
agcatcccag tagtcggcgg gccgctcgac gaactccggc atgtgcccgg attcggcgtg   13140
caagacttca tccatgtcgc gggcatactt gccttcgcgc tggatgtagt cggccttggc   13200
cctggccgat tggccgcccg acctgctgcc ggttttcgcc gtaaggtgat aaatcgccat   13260
gctgcctcgc tgttgctttt gctttcggc tccatgcaat ggccctcgga gagcgcaccg    13320
cccgaagggt ggccgttagg ccagtttctc gaagagaaac cggtaagtgc gccctccct    13380 acaaagtagg gtcgggattg ccgccgctgt gcctccatga tagcctacga gacagcacat   13440
taacaatggg gtgtcaagat ggttaagggg agcaacaagg cggcggatcg gctggccaag   13500
ctcgaagaac aacgagcgcg aatcaatgcc gaaattcagc gggtgcgggc aagggaacag   13560
cagcaagagc gcaagaacga aacaaggcgc aaggtgctgg tggggccat gattttggcc     13620 aaggtgaaca gcagcgagtg gccggaggat cggctcatgg cggcaatgga tgcgtacctt   13680
gaacgcgacc acgaccgcgc cttgttcggt ctgccgccac gccagaagga tgagccgggc   13740
tgaatgatcg accgagacag gccctgcggg gctgcacacg cgcccccacc cttcgggtag   13800
ggggaaaggc cgctaaagcg gctaaaagcg ctccagcgta tttctgcggg gtttggtgtg   13860
gggtttagcg ggctttgccc gccttccccc ctgccgcgca gcggtgggc ggtgtgtagc    13920 ctagcgcagc gaatagacca gctatccggc ctctggccgg gcatattggg caagggcagc   13980
agcgccccac aagggcgctg ataaccgcgc ctagtggatt attcttagat aatcatggat   14040
ggatttttcc aacaccccgc cagccccgc ccctgctggg tttgcaggtt tggggcgtg    14100 acagttattg caggggttcg tgacagttat tgcaggggg cgtgacagtt attgcagggg   14160
ttcgtgacag ttagtacggg agtgacgggc actggctggc aatgtctagc aacggcaggc   14220
atttcggctg agggtaaaag aactttccgc taagcgatag actgtatgta aacacagtat   14280
tgcaaggacg cggaacatgc ctcatgtggc ggccaggacg ccagccggg atcgggatac    14340 tggtcgttac cagagccacc gacccgagca aaccttctc tatcagatcg ttgacgagta    14400
ttacccggca ttcgctgcgc ttatggcaga gcagggaaag gaattgccgg gctatgtgca   14460
acgggaattt gaagaatttc tccaatgcgg cggctggag catggctttc tacgggttcg    14520
ctgcgagtct tgccacgccg agcacctggt cgctttcagc tgtaagcgtc gcggtttctg   14580
cccgagctgt ggggcgcggc ggatggccga aagtgccgcc ttgctggttg atgaagtact   14640
gcctgaacaa cccatgcgtc agtgggtgtt gagcttcccg tttcagctgc gtttcctgtt   14700
```

```
tggggtcgtt tgcgggaagg ggcggaatcc tacgctaagg ctttggccag cgatattctc    14760
cggtgagatt gatgtgttcc caggggatag agaagtcgc ttgatatcta gtatgacgtc     14820
tgtcgcacct gcttgatcgc ggcccaaggg ttggtttgcg cattcacagt tctccgcaag    14880
aattgattgg ctccaattct tggagtggtg aatccgttag cgaggtgccg ccggcttcca    14940
ttcaggtcga ggtggcccgg ctccatgcac cgcgacgcaa cgcggggagg cagacaaggt    15000 ataggggcggc gcctacaatc catgccaacc cgttccatgt gctcgccgag gcggcataaa   15060
tcgccgtgac gatcagcggt ccagtgatcg aagttaggct ggtaagagcc gcgagcgatc    15120
cttgaagctg tccctgatgg tcgtcatcta cctgcctgga cagcatggcc tgcaacgcgg    15180
gcatcccgat gccgccggaa gcgagaagaa tcataatggg gaaggccatc cagcctcgcg    15240
tcgcgaacgc cagcaagacg tagcccagcg cgtcggccgc catgccggcg ataatggcct    15300
gcttctcgcc gaaacgtttg gtggcgggac cagtgacgaa ggcttgagcg agggcgtgca    15360
agattccgaa taccgcaagc gacaggccga tcatcgtcgc gctccagcga aagcggtcct    15420
cgccgaaaat gacccagagc gctgccggca cctgtcctac gagttgcatg ataaagaaga    15480
cagtcataag tgcggcgacg atagtcatgc cccgcgccca ccggaaggag ctgactgggt    15540
tgaaggctct caagggcatc ggtcgacgct ctcccttatg cgactcctgc attaggaagc    15600
agcccagtag taggttgagg ccgttgagca ccgccgccgc aaggaatggt gcatgcaagg    15660
agatggcgcc caacagtccc ccggccacgg ggcctgccac catacccacg ccgaaacaag    15720
cgctcatgag cccgaagtgg cgagcccgat cttcccatc ggtgatgtcg gcgatatagg     15780
cgccagcaac cgcacctgtg gcgccggtga tgccggccac gatgcgtccg gcgtagagga    15840
tccacaggac gggtgtggtc gccatgatcg cgtagtcgat agtggctcca agtagcgaag    15900
cgagcaggac tgggcggcgg ccaaagcggt cggacagtgc tccgagaacg ggtgcgcata    15960
gaaattgcat caacgcatat agcgctagca gcacgccata gtgactggcg atgctgtcgg    16020
aatggacgat atcccgcaag aggcccggca gtaccggcat aaccaagcct atgcctacag    16080
catccagggt gacggtgccg aggatgacga tgagcgcatt gttagatttc atacacggtg    16140
cctgactgcg ttagcaattt aactgtgata aactaccgca ttaaagctta tcgatgataa    16200
gctgtcaaac atga                                                      16214
```

<210> SEQ ID NO 9
<211> LENGTH: 427
<212> TYPE: PRT
<213> ORGANISM: Pantoea ananatis

<400> SEQUENCE: 9

```
Met Ala Asp Thr Lys Ala Lys Leu Thr Leu Asn Gly Asp Thr Ala Val
 1               5                  10                  15

Glu Leu Asp Val Leu Lys Gly Thr Leu Gly Gln Asp Val Ile Asp Ile
             20                  25                  30

Arg Thr Leu Gly Ser Lys Gly Val Phe Thr Phe Asp Pro Gly Phe Thr
         35                  40                  45

Ser Thr Ala Ser Cys Glu Ser Lys Ile Thr Phe Ile Asp Gly Asp Glu
     50                  55                  60

Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95
```

```
Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
            115                 120                 125

Ser His Pro Met Ala Val Met Cys Gly Ile Thr Gly Ala Leu Ala Ala
            130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
            195                 200                 205

Pro Tyr Glu Val Asn Pro Ile Leu Glu Arg Ala Met Asp Arg Ile Leu
            210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
            275                 280                 285

Phe Arg Arg Ala Lys Asp Lys Asn Asp Ser Phe Arg Leu Met Gly Phe
            290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
            355                 360                 365

Ile Leu Lys Ala Met Gly Ile Pro Ser Ser Met Phe Thr Val Ile Phe
            370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425

<210> SEQ ID NO 10
<211> LENGTH: 447
<212> TYPE: PRT
<213> ORGANISM: Pantoea ananatis

<400> SEQUENCE: 10

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45
```

```
Ser Leu Leu Glu Arg Leu Val Glu Pro Glu Arg Val Ile Gln Phe Arg
 50                  55                  60

Val Val Trp Val Asp Asp Arg Asn Gln Ile Gln Val Asn Arg Ala Trp
 65                  70                  75                  80

Arg Val Gln Phe Ser Ser Ala Ile Gly Pro Tyr Lys Gly Gly Met Arg
                 85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Pro Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 11
<211> LENGTH: 883
```

```
<212> TYPE: PRT
<213> ORGANISM: Pantoea ananatis

<400> SEQUENCE: 11

Met Asn Glu Gln Tyr Ser Ala Leu Arg Ser Asn Val Ser Met Leu Gly
 1               5                  10                  15

Lys Val Leu Gly Glu Thr Ile Lys Asp Ala Leu Gly Glu His Ile Leu
             20                  25                  30

Glu Arg Val Glu Thr Ile Arg Lys Leu Ser Lys Ser Ser Arg Ala Gly
         35                  40                  45

Asn Asp Ala Asn Arg Gln Glu Leu Leu Thr Thr Leu Gln Asn Leu Ser
     50                  55                  60

Asn Asp Glu Leu Leu Pro Val Ala Arg Ala Phe Ser Gln Phe Leu Asn
 65                  70                  75                  80

Leu Ala Asn Thr Ala Glu Gln Tyr His Ser Ile Ser Pro Lys Gly Glu
                 85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400
```

-continued

Arg His Thr Glu Ala Leu Gly Glu Leu Thr Arg Tyr Leu Gly Ile Gly
            405                 410                 415
Asp Tyr Glu Ser Trp Ser Glu Ala Asp Lys Gln Ala Phe Leu Ile Arg
            420                 425                 430
Glu Leu Asn Ser Lys Arg Pro Leu Leu Pro Arg Asn Trp Gln Pro Ser
            435                 440                 445
Ala Glu Thr Arg Glu Val Leu Asp Thr Cys Gln Val Ile Ala Glu Ala
            450                 455                 460
Pro Gln Gly Ser Ile Ala Ala Tyr Val Ile Ser Met Ala Lys Thr Pro
465                 470                 475                 480
Ser Asp Val Leu Ala Val His Leu Leu Leu Lys Glu Ala Gly Ile Gly
            485                 490                 495
Phe Ala Met Pro Val Ala Pro Leu Phe Glu Thr Leu Asp Asp Leu Asn
            500                 505                 510
Asn Ala Asn Asp Val Met Thr Gln Leu Leu Asn Ile Asp Trp Tyr Arg
            515                 520                 525
Gly Leu Ile Gln Gly Lys Gln Met Val Met Ile Gly Tyr Ser Asp Ser
            530                 535                 540
Ala Lys Asp Ala Gly Val Met Ala Ala Ser Trp Ala Gln Tyr Gln Ala
545                 550                 555                 560
Gln Asp Ala Leu Ile Lys Thr Cys Glu Lys Ala Gly Ile Glu Leu Thr
            565                 570                 575
Leu Phe His Gly Arg Gly Gly Ser Ile Gly Arg Gly Gly Ala Pro Ala
            580                 585                 590
His Ala Ala Leu Leu Ser Gln Pro Pro Gly Ser Leu Lys Gly Gly Leu
            595                 600                 605
Arg Val Thr Glu Gln Gly Glu Met Ile Arg Phe Lys Tyr Gly Leu Pro
            610                 615                 620
Glu Ile Thr Val Ser Ser Leu Ser Leu Tyr Thr Gly Ala Ile Leu Glu
625                 630                 635                 640
Ala Asn Leu Leu Pro Pro Pro Glu Pro Lys Glu Ser Trp Arg Arg Ile
            645                 650                 655
Met Asp Glu Leu Ser Val Ile Ser Cys Asp Val Tyr Arg Gly Tyr Val
            660                 665                 670
Arg Glu Asn Lys Asp Phe Val Pro Tyr Phe Arg Ser Ala Thr Pro Glu
            675                 680                 685
Gln Glu Leu Gly Lys Leu Pro Leu Gly Ser Arg Pro Ala Lys Arg Arg
            690                 695                 700
Pro Thr Gly Gly Val Glu Ser Leu Arg Ala Ile Pro Trp Ile Phe Ala
705                 710                 715                 720
Trp Thr Gln Asn Arg Leu Met Leu Pro Ala Trp Leu Gly Ala Gly Thr
            725                 730                 735
Ala Leu Gln Lys Val Val Glu Asp Gly Lys Gln Ser Glu Leu Glu Ala
            740                 745                 750
Met Cys Arg Asp Trp Pro Phe Phe Ser Thr Arg Leu Gly Met Leu Glu
            755                 760                 765
Met Val Phe Ala Lys Ala Asp Leu Trp Leu Ala Glu Tyr Tyr Asp Gln
            770                 775                 780
Arg Leu Val Asp Lys Ala Leu Trp Pro Leu Gly Lys Glu Leu Arg Asn
785                 790                 795                 800
Leu Gln Glu Glu Asp Ile Lys Val Val Leu Ala Ile Ala Asn Asp Ser
            805                 810                 815

-continued

```
His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly

<210> SEQ ID NO 12
<211> LENGTH: 6035
<212> TYPE: DNA
<213> ORGANISM: Artificial Sequence
<220> FEATURE:
<223> OTHER INFORMATION: plasmid pSTVCB
<220> FEATURE:
<221> NAME/KEY: CDS
<222> LOCATION: (2129)..(3439)

<400> SEQUENCE: 12
cgtatggcaa tgaaagacgg tgagctggtg atatgggata gtgttcaccc ttgttacacc        60
gttttccatg agcaaactga acgttttca tcgctctgga gtgaatacca cgacgatttc       120
cggcagtttc tacacatata ttcgcaagat gtggcgtgtt acggtgaaaa cctggcctat       180
ttccctaaag ggtttattga gaatatgttt ttcgtctcag ccaatccctg ggtgagtttc       240
accagttttg atttaaacgt ggccaatatg acaacttct tcgcccccgt tttcaccatg        300
ggcaaatatt atacgcaagg cgacaaggtg ctgatgccgc tggcgattca ggttcatcat       360
gccgtctgtg atggcttcca tgtcggcaga atgcttaatg aattacaaca gtactgcgat       420
gagtggcagg gcggggcgta atttttttaa ggcagttatt ggtgccctta aacgcctggt       480
gctacgcctg aataagtgat aataagcgga tgaatggcag aaattcgaaa gcaaattcga       540
cccggtcgtc ggttcagggc agggtcgtta atagccgct tatgtctatt gctggtttac        600
cggtttattg actaccggaa gcagtgtgac cgtgtgcttc tcaaatgcct gaggccagtt       660
tgctcaggct ctccccgtgg aggtaataat tgacgatatg atcatttatt ctgcctccca       720
gagcctgata aaaacggtta gcgcttcgtt aatacagatg taggtgttcc acagggtagc       780
cagcagcatc ctgcgatgca gatccggaac ataatggtgc agggcgcttg tttcggcgtg       840
ggtatggtgg caggccccgt ggccggggga ctgttgggcg ctgccggcac ctgtcctacg       900
agttgcatga taaagaagac agtcataagt gcggcgacga tagtcatgcc ccgcgcccac       960
cggaaggagc taccgacag cggtgcggac tgttgtaact cagaataaga aatgaggccg      1020
ctcatggcgt tccaatacgc aaaccgcctc tccccgcgcg ttggccgatt cattaatgca      1080
gctggcacga caggtttccc gactggaaag cgggcagtga gcgcaacgca attaatgtga      1140
gttagctcac tcattaggca ccccaggctt tacactttat gcttccggct cgtatgttgt      1200
gtggaattgt gagcggataa caatttcaca caggaaacag ctatgaccat gattacgcca      1260
agcttgcatg cctgcaggtc gactctagag gatccgtcga caatagcctg aatctgttct      1320
ggtcgaacct tggaaggtcc gcagccgaaa cggccgtcgc cagggatgaa ctcagagggc      1380
agggtgggga agtcggtcat gtcttcgggc aactttctgc gcttggaagt aaaagggcca      1440
gggatcgtta acgatctgac ccaacaacta taaccctgaa gctgtcagtt cctagcaccc      1500
tagattcttc acgcagtctc ccaaacgatg aaaaacgccc aaaactggcg acaccgaact      1560
```

```
attgaaaacg cgggggttag ttgaccagcc accaatttgg gggtagttca aagttttgca    1620
aagttttcaa tttctaggtt gttaatatcc cctgaggttg cgttataggg tggcgaattg    1680 catgggaaa gctactcggc acccatcctt gtcgcgtgca tcacaaactt tgctaaactg    1740
tgtaccagtc cacttattgt gggatttta atgcctaaaa ggccagcatt ttcaccctct    1800
agcggggttg aatgctggcc ttgagggtgc agaactaaat agcagcacat cggcacaatt    1860
gatctgagtt ctattggcgt gaccgtggct actgattacg gtggctgtgg gtggtcggga    1920
atgatgtaac caacgtgatt gtggggaat tggctctcac ttcggatatg ctaaaccgc     1980 atttatcggt atagcgtgtt aaccggacca gattgggaaa gaatgtgtc gagtaacaaa    2040 aactgacatg cgcttggcgc atcccagttg gtaagaataa acgggactac ttccgtaatc    2100
cggaagagtt tttttccgaa caaat atg ttt gaa agg gat atc gtg gct act     2152
                            Met Phe Glu Arg Asp Ile Val Ala Thr
                             1               5
```

| gat | aac | aac | aag | gct | gtc | ctg | cac | tac | ccc | ggt | ggc | gag | ttc | gaa | atg | 2200 |
|-----|-----|-----|-----|-----|-----|-----|-----|-----|-----|-----|-----|-----|-----|-----|-----|------|
| Asp | Asn | Asn | Lys | Ala | Val | Leu | His | Tyr | Pro | Gly | Gly | Glu | Phe | Glu | Met |      |
| 10  |     |     |     | 15  |     |     |     |     | 20  |     |     |     |     | 25  |     |      |

| gac | atc | atc | gag | gct | tct | gag | ggt | aac | aac | ggt | gtt | gtc | ctg | ggc | aag | 2248 |
|-----|-----|-----|-----|-----|-----|-----|-----|-----|-----|-----|-----|-----|-----|-----|-----|------|
| Asp | Ile | Ile | Glu | Ala | Ser | Glu | Gly | Asn | Asn | Gly | Val | Val | Leu | Gly | Lys |      |
|     |     |     | 30  |     |     |     |     | 35  |     |     |     |     | 40  |     |     |      |

| atg | ctg | tct | gag | act | gga | ctg | atc | act | ttt | gac | cca | ggt | tat | gtg | agc | 2296 |
|-----|-----|-----|-----|-----|-----|-----|-----|-----|-----|-----|-----|-----|-----|-----|-----|------|
| Met | Leu | Ser | Glu | Thr | Gly | Leu | Ile | Thr | Phe | Asp | Pro | Gly | Tyr | Val | Ser |      |
|     |     | 45  |     |     |     |     | 50  |     |     |     |     | 55  |     |     |     |      |

| act | ggc | tcc | acc | gag | tcg | aag | atc | acc | tac | atc | gat | ggc | gat | gcg | gga | 2344 |
|-----|-----|-----|-----|-----|-----|-----|-----|-----|-----|-----|-----|-----|-----|-----|-----|------|
| Thr | Gly | Ser | Thr | Glu | Ser | Lys | Ile | Thr | Tyr | Ile | Asp | Gly | Asp | Ala | Gly |      |
|     | 60  |     |     |     |     | 65  |     |     |     |     | 70  |     |     |     |     |      |

| atc | ctg | cgt | tac | cgc | ggc | tat | gac | atc | gct | gat | ctg | gct | gag | aat | gcc | 2392 |
|-----|-----|-----|-----|-----|-----|-----|-----|-----|-----|-----|-----|-----|-----|-----|-----|------|
| Ile | Leu | Arg | Tyr | Arg | Gly | Tyr | Asp | Ile | Ala | Asp | Leu | Ala | Glu | Asn | Ala |      |
| 75  |     |     |     |     | 80  |     |     |     |     | 85  |     |     |     |     |     |      |

| acc | ttc | aac | gag | gtt | tct | tac | cta | ctt | atc | aac | ggt | gag | cta | cca | acc | 2440 |
|-----|-----|-----|-----|-----|-----|-----|-----|-----|-----|-----|-----|-----|-----|-----|-----|------|
| Thr | Phe | Asn | Glu | Val | Ser | Tyr | Leu | Leu | Ile | Asn | Gly | Glu | Leu | Pro | Thr |      |
| 90  |     |     |     | 95  |     |     |     |     | 100 |     |     |     |     | 105 |     |      |

| cca | gat | gag | ctt | cac | aag | ttt | aac | gac | gag | att | cgc | cac | cac | acc | ctt | 2488 |
|-----|-----|-----|-----|-----|-----|-----|-----|-----|-----|-----|-----|-----|-----|-----|-----|------|
| Pro | Asp | Glu | Leu | His | Lys | Phe | Asn | Asp | Glu | Ile | Arg | His | His | Thr | Leu |      |
|     |     |     |     | 110 |     |     |     |     | 115 |     |     |     |     | 120 |     |      |

| ctg | gac | gag | gac | ttc | aag | tcc | cag | ttc | aac | gtg | ttc | cca | cgc | gac | gct | 2536 |
|-----|-----|-----|-----|-----|-----|-----|-----|-----|-----|-----|-----|-----|-----|-----|-----|------|
| Leu | Asp | Glu | Asp | Phe | Lys | Ser | Gln | Phe | Asn | Val | Phe | Pro | Arg | Asp | Ala |      |
|     |     | 125 |     |     |     |     | 130 |     |     |     |     | 135 |     |     |     |      |

| cac | cca | atg | gca | acc | ttg | gct | tcc | tcg | gtt | aac | att | ttg | tct | acc | tac | 2584 |
|-----|-----|-----|-----|-----|-----|-----|-----|-----|-----|-----|-----|-----|-----|-----|-----|------|
| His | Pro | Met | Ala | Thr | Leu | Ala | Ser | Ser | Val | Asn | Ile | Leu | Ser | Thr | Tyr |      |
|     | 140 |     |     |     |     | 145 |     |     |     |     | 150 |     |     |     |     |      |

| tac | cag | gat | cag | ctg | aac | cca | ctc | gat | gag | gca | cag | ctt | gat | aag | gca | 2632 |
|-----|-----|-----|-----|-----|-----|-----|-----|-----|-----|-----|-----|-----|-----|-----|-----|------|
| Tyr | Gln | Asp | Gln | Leu | Asn | Pro | Leu | Asp | Glu | Ala | Gln | Leu | Asp | Lys | Ala |      |
| 155 |     |     |     |     | 160 |     |     |     |     | 165 |     |     |     |     |     |      |

| acc | gtt | cgc | ctc | atg | gca | aag | gtt | cca | atg | ctg | gct | gcg | tac | gca | cac | 2680 |
|-----|-----|-----|-----|-----|-----|-----|-----|-----|-----|-----|-----|-----|-----|-----|-----|------|
| Thr | Val | Arg | Leu | Met | Ala | Lys | Val | Pro | Met | Leu | Ala | Ala | Tyr | Ala | His |      |
| 170 |     |     |     | 175 |     |     |     |     | 180 |     |     |     |     | 185 |     |      |

| cgc | gca | cgc | aag | ggt | gct | cct | tac | atg | tac | cca | gac | aac | tcc | ctc | aac | 2728 |
|-----|-----|-----|-----|-----|-----|-----|-----|-----|-----|-----|-----|-----|-----|-----|-----|------|
| Arg | Ala | Arg | Lys | Gly | Ala | Pro | Tyr | Met | Tyr | Pro | Asp | Asn | Ser | Leu | Asn |      |
|     |     |     |     | 190 |     |     |     |     | 195 |     |     |     |     | 200 |     |      |

| gcg | cgt | gag | aac | ttc | ctg | cgc | atg | atg | ttc | ggt | tac | cca | acc | gag | cca | 2776 |
|-----|-----|-----|-----|-----|-----|-----|-----|-----|-----|-----|-----|-----|-----|-----|-----|------|
| Ala | Arg | Glu | Asn | Phe | Leu | Arg | Met | Met | Phe | Gly | Tyr | Pro | Thr | Glu | Pro |      |
|     |     | 205 |     |     |     |     | 210 |     |     |     |     | 215 |     |     |     |      |

| tac | gag | atc | gac | cca | atc | atg | gtc | aag | gct | ctg | gac | aag | ctg | ctc | atc | 2824 |
|-----|-----|-----|-----|-----|-----|-----|-----|-----|-----|-----|-----|-----|-----|-----|-----|------|
| Tyr | Glu | Ile | Asp | Pro | Ile | Met | Val | Lys | Ala | Leu | Asp | Lys | Leu | Leu | Ile |      |
|     | 220 |     |     |     |     | 225 |     |     |     |     | 230 |     |     |     |     |      |

| ctg | cac | gct | gac | cac | gag | cag | aac | tgc | tcc | acc | tcc | acc | gtt | cgt | atg | 2872 |
|-----|-----|-----|-----|-----|-----|-----|-----|-----|-----|-----|-----|-----|-----|-----|-----|------|

```
Leu His Ala Asp His Glu Gln Asn Cys Ser Thr Ser Thr Val Arg Met
    235                 240                 245 atc ggt tcc gca cag gcc aac atg ttt gtc tcc atc gct ggt ggc atc      2920
Ile Gly Ser Ala Gln Ala Asn Met Phe Val Ser Ile Ala Gly Gly Ile
250                 255                 260                 265 aac gct ctg tcc ggc cca ctg cac ggt ggc gca aac cag gct gtt ctg      2968
Asn Ala Leu Ser Gly Pro Leu His Gly Gly Ala Asn Gln Ala Val Leu
                270                 275                 280 gag atg ctc gaa gac atc aag aac aac cac ggt ggc gac gca acc gcg      3016
Glu Met Leu Glu Asp Ile Lys Asn Asn His Gly Gly Asp Ala Thr Ala
            285                 290                 295 ttc atg aac aag gtc aag aac aag gaa gac ggc gtc cgc ctc atg ggc      3064
Phe Met Asn Lys Val Lys Asn Lys Glu Asp Gly Val Arg Leu Met Gly
        300                 305                 310 ttc gga cac cgc gtt tac aag aac tac gat cca cgt gca gca atc gtc      3112
Phe Gly His Arg Val Tyr Lys Asn Tyr Asp Pro Arg Ala Ala Ile Val
    315                 320                 325 aag gag acc gca cac gag atc ctc gag cac ctc ggt ggc gac gat ctt      3160
Lys Glu Thr Ala His Glu Ile Leu Glu His Leu Gly Gly Asp Asp Leu
330                 335                 340                 345 ctg gat ctg gca atc aag ctg gaa gaa att gca ctg gct gat gat tac      3208
Leu Asp Leu Ala Ile Lys Leu Glu Glu Ile Ala Leu Ala Asp Asp Tyr
                350                 355                 360 ttc atc tcc cgc aag ctc tac ccg aac gta gac ttc tac acc ggc ctg      3256
Phe Ile Ser Arg Lys Leu Tyr Pro Asn Val Asp Phe Tyr Thr Gly Leu
            365                 370                 375 atc tac cgc gca atg ggc ttc cca act gac ttc ttc acc gta ttg ttc      3304
Ile Tyr Arg Ala Met Gly Phe Pro Thr Asp Phe Phe Thr Val Leu Phe
        380                 385                 390 gca atc ggt cgt ctg cca gga tgg atc gct cac tac cgc gag cag ctc      3352
Ala Ile Gly Arg Leu Pro Gly Trp Ile Ala His Tyr Arg Glu Gln Leu
    395                 400                 405 ggt gca gca ggc aac aag atc aac cgc cca cgc cag gtc tac acc ggc      3400
Gly Ala Ala Gly Asn Lys Ile Asn Arg Pro Arg Gln Val Tyr Thr Gly
410                 415                 420                 425 aag gaa tcc cgc aag ttg gtt cct cgc gag gag cgc taaatttagc           3446
Lys Glu Ser Arg Lys Leu Val Pro Arg Glu Glu Arg
                430                 435 ggatgattct cgttcaactt cggccgaagc cacttcgtct gtcataatga cagggatggt    3506
ttcggccgtt tttgcatgaa accaaaaaat acgattttca aggagcatgt acagcacatg    3566
gaaaagccac agattgagct accggtcggt ccagcaccgg aagatctcgt aatctctgac    3626
atcatcgttg gcgaaggcgc agaagcccgc ccaggcggag aagttgaggt ccactatgtg    3686
ggcgttgacc ttgaaaccgg cgaggagttt gactcttcct gggatcgtgg acagaccagc    3746
cagttcccac tcaacggcct cattgcaggt tggcaagaag gaattccagg catgaaggtc    3806
ggcggacgtc gtcagctgac cattccgcca gaggctgctt acggccctga gggttccggc    3866
cacccactgt ctggccgtac cctggtgttc atcatcgatt tgatcagcgc ataatttct    3926 ttactgcgct aaacgctcaa atcgtgtgaa gcgactgtcg cgtcctgccc tctccggatt    3986
gttatccaat tcggagaggg cgttgctgat tgtgccgaga atttcttcaa caaagtgctc    4046
ggtttcggcg acgatcccgt cgataagccc ttggcttaaa agtgcgtgcg cctgcacgcc    4106
ttgtcgctct atgatttccg cggcgtggtt ggtgtcgcgg aagaggatgg ccgaggcgcc    4166
ctctggaggc aatgcggaca gccacgcgtt ttcggccgcg tagaccagat cggcgggcag    4226
catggccagc gcgccaccgc caacgccctg accaataatg accgaaacgg tggggagggg    4286
```

-continued

```
agcgtcgata agcttgcatg cctgcaggtc gactctagag gatccccggg taccgagctc      4346
gaattcactg gccgtcgttt tacaacgtcg tgactgggaa acccctggcg ttacccaact      4406
taatcgcctt gcagcacatc ccctttcgc cagctggcgt aatagcgaag aggcccgcac       4466
cgatcgccct tcccaacagt tgcgcagcct gaatggcgaa tgagcttatc gatgataagc      4526
tgtcaaacat gagaattaca acttatatcg tatggggctg acttcaggtg ctacatttga      4586
agagataaat tgcactgaaa tctagaaata ttttatctga ttaataagat gatcttcttg      4646
agatcgtttt ggtctgcgcg taatctcttg ctctgaaaac gaaaaaaccg ccttgcaggg      4706
cggttttttcg aaggttctct gagctaccaa ctctttgaac cgaggtaact ggcttggagg     4766
agcgcagtca ccaaaacttg tcctttcagt ttagccttaa ccggcgcatg acttcaagac      4826
taactcctct aaatcaatta ccagtggctg ctgccagtgg tgcttttgca tgtctttccg      4886
ggttggactc aagacgatag ttaccggata aggcgcagcg gtcggactga acgggggggtt    4946
cgtgcataca gtccagcttg gagcgaactg cctacccgga actgagtgtc aggcgtggaa      5006
tgagacaaac gcggccataa cagcggaatg acaccggtaa accgaaaggc aggaacagga     5066
gagcgcacga gggagccgcc aggggaaacg cctggtatct ttatagtcct gtcgggtttc     5126
gccaccactg atttgagcgt cagatttcgt gatgcttgtc aggggggcgg agcctatgga     5186
aaaacggctt tgccgcggcc ctctcacttc cctgttaagt atcttcctgg catcttccag     5246
gaaatctccg ccccgttcgt aagccatttc cgctcgccgc agtcgaacga ccgagcgtag     5306
cgagtcagtg agcgaggaag cggaatatat cctgtatcac atattctgct gacgcaccgg     5366
tgcagccttt tttctcctgc cacatgaagc acttcactga caccctcatc agtgccaaca     5426
tagtaagcca gtatacactc cgctagcgct gatgtccggc ggtgcttttg ccgttacgca     5486
ccaccccgtc agtagctgaa caggagggac agctgataga aacagaagcc actggagcac     5546
ctcaaaaaca ccatcataca ctaaatcagt aagttggcag catcacccga cgcactttgc     5606
gccgaataaa tacctgtgac ggaagatcac ttcgcagaat aaataaatcc tggtgtccct     5666
gttgataccg ggaagccctg gccaactttt tggcgaaaat gagacgttga tcggcacgta     5726
agaggttcca actttcacca taatgaaata agatcactac cgggcgtatt ttttgagtta     5786
tcgagatttt caggagctaa ggaagctaaa atggagaaaa aaatcactgg atataccacc     5846
gttgatatat cccaatggca tcgtaaagaa catttttgagg catttcagtc agttgctcaa     5906
tgtacctata accagaccgt tcagctggat attacggcct ttttaaagac cgtaaagaaa     5966
aataagcaca gttttatcc ggcctttatt cacattcttg cccgcctgat gaatgctcat      6026
ccggaattt                                                             6035
```

<210> SEQ ID NO 13
<211> LENGTH: 437
<212> TYPE: PRT
<213> ORGANISM: Brevibacterium lactofermentum

<400> SEQUENCE: 13

```
Met Phe Glu Arg Asp Ile Val Ala Thr Asp Asn Asn Lys Ala Val Leu
 1               5                  10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60
```

```
Ile Thr Tyr Ile Asp Gly Asp Ala Gly Ile Leu Arg Tyr Arg Gly Tyr
 65                  70                  75                  80

Asp Ile Ala Asp Leu Ala Glu Asn Ala Thr Phe Asn Glu Val Ser Tyr
             85                  90                  95

Leu Leu Ile Asn Gly Glu Leu Pro Thr Pro Asp Glu Leu His Lys Phe
        100                 105                 110

Asn Asp Glu Ile Arg His His Thr Leu Leu Asp Glu Asp Phe Lys Ser
    115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Asn Asn His Gly Gly Asp Ala Thr Ala Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Lys Glu Ser Arg Lys Leu Val
            420                 425                 430

Pro Arg Glu Glu Arg
            435
```